United States Patent [19]
Denny et al.

[11] Patent Number: 6,071,908
[45] Date of Patent: Jun. 6, 2000

[54] RADIATION-ACTIVATED CYTOTOXIN THERAPY OF NEOPLASTIC DISEASE

[75] Inventors: William A. Denny; Moena Tercel; William R. Wilson, all of Auckland, New Zealand

[73] Assignee: Auckland Uniservices Limited, Auckland, New Zealand

[21] Appl. No.: 09/011,528

[22] PCT Filed: Aug. 19, 1996

[86] PCT No.: PCT/NZ96/00085

§ 371 Date: May 7, 1998

§ 102(e) Date: May 7, 1998

[87] PCT Pub. No.: WO97/07101

PCT Pub. Date: Feb. 27, 1997

[30] Foreign Application Priority Data

Aug. 18, 1995 [NZ] New Zealand ............................ 272815

[51] Int. Cl.[7] .......................... A61K 31/14; A61K 31/40; A61K 31/435; C07D 219/04; C07D 209/42; C07C 225/34

[52] U.S. Cl. ...................... 514/232.8; 514/290; 514/399; 514/400; 514/414; 514/424; 514/501; 514/643; 544/126; 546/6; 546/102; 546/104; 548/327.1; 548/455; 548/512; 552/301; 564/282; 564/284; 556/146

[58] Field of Search ................................ 548/327.1, 455, 548/512; 544/126; 546/102, 104, 6; 564/282, 284; 552/301; 556/146; 514/399, 400, 414, 424, 290, 232.8, 501, 643

[56] References Cited

PUBLICATIONS

Journal of the American Chemical Society, vol. 112, No. 24, Nov. 21, 1990, DC US, pp. 8961–8971, XP002019527 Dale L. Boger et al: "Duocarmycin–pyrindamycin DNA alkylation properies an identification, systhesis, and evaluation of agents incorporating the pharmacophore of the duocarmyci–pyrindamycin alkylation subunit." See the whole document.

Journal of Medicinal Chemistry, vol. 35, No. 14, Jul. 10, 1992, Washington US, pp. 2711–2712, XP002019528 Sei–Ichi Nishimoto et al: "1–(5"–flourouracil, a novel N(1)–C(5)–linked dimer that releases 5–flourouracil by radiation activation under hypoxix conditions" cited in the application see whole document.

Journal of Medicinal Chemistry, vol. 36, No. 17, Aug. 20, 1993, Washington US, pp. 2578–2579, XP002019529 Moana Tercel et al: "Nitrobenzyl mustard quarternary salts: a new class of hypoxia–selective cytotoxins showing very high in vitro selectivity" cited in the application see whole document.

Journal of Medicinal Chemistry, vol. 36, No. 13, Jun. 25, 1993, Washington US, pp. 1839–1846, XP002019530 David C> Ware et al: "Hypoxia–selective antitumar agents. 7. Metal complexes of aliphatic mustards as a new class of hypoxia–selective cytotixins. Synthesis and evaluation of cobalt(III) complexes of bidentate mustards" cited in the application see the whole document.

*Primary Examiner*—Floyd D. Higel
*Attorney, Agent, or Firm*—Nixon & Vanderhye

[57] ABSTRACT

A method of treating neoplastic disease wherein a patient in need of such treatment is administered an effective amount of a radiation-activated cytotoxin prodrug (RACP) which has low toxicity, which is reducible by reducing agents generated by the radiolysis of water and which, upon reduction, releases a sufficient amount of a cytotoxic effector of sufficient cytotoxic potency to kill tumor cells. The tumor cells are irradiated with ionizing radiation to reduce the prodrug which is present at the locus of the tumor cells to release the cytotoxic effector.

25 Claims, 5 Drawing Sheets

RADIATION-ACTIVATED CYTOTOXIN THERAPY OF NEOPLASTIC DISEASE

This application is a 371 of PCT/NZ96/00085 filed Aug. 19, 1996.

This invention relates to cancer therapy. More particularly, it relates to the use of ionising radiation to activate drugs to form cytotoxic species in hypoxic microenvironments, to methods of treating neoplastic disease, to a new class of compounds for use in such treatments and to methods for preparing these compounds.

BACKGROUND TO THE INVENTION

Ionising radiation is widely used to treat neoplastic disease, but its effectiveness appears often to be limited by the presence of radioresistant hypoxic cells in tumours. At present there is no generally-useful method for eliminating these hypoxic tumour cells. One approach, being evaluated clinically at present, is the use of compounds which are selectively toxic to cells under hypoxic conditions. The most important compounds of this type are known as bioreductive drugs (BD) because they are activated metabolically by enzymatic reduction to form cytotoxic products under hypoxic conditions. In general, the selectivity of these compound, to hypoxic cells is a consequence of reoxidation of the initial one-electron reduction product by dioxygen, resulting in futile redox cycling and suppression of net reduction in oxygenated tissue.

The mechanism of activation of most BD is as follows:

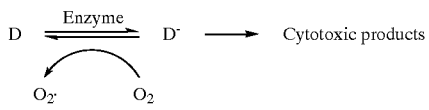

BD are however likely to have two main limitations in clinical use.

The first of these is that enzymatic activation of BD is not restricted exclusively to hypoxic environments in tumours, and these drugs will therefore have some toxic effect against normal, well-oxygenated tissues. In particular, reductive activation by oxygen-insensitive pathways (obligate 2-electron reduction, which bypasses the $O_2$-sensitive intermediate) may sometimes be a limitation.

A second limitation of BD is that, to be effective, enzymes capable of activating the bioreductive drug must be expressed at a high level in the tumour. This is not a condition which will be met by all tumours.

An alternative approach involving activation of a prodrug was reported by Nishimoto et al in *J. Med. Chem* 35:2712–2715 (1992). In this approach, radiolytic activation of a 5-fluorouracil (5-FU) dimer was suggested as a radiosensitisation strategy in mice. However, it is apparent that radiolytic activation of the reported 5-FU dimer would not be clinically effective as the yield of cytotoxin was too low (a theoretical maximum yield in the order of 2 $\mu$mol/kg at the radiation dose used (20Gy)).

SUMMARY OF THE INVENTION

It is therefore an object of the invention to provide a method of effectively treating neoplastic disease which is not subject to the limitations of BD therapy, or at least to provide the public with a useful choice.

Accordingly in a first aspect, the invention provides a method of treating neoplastic disease which comprises the steps of:

(a) administering to a patient in need of such treatment an effective amount of a radiation-activated cytotoxin prodrug (RACP) which has low toxicity, which can be reduced by reducing agents generated by the radiolysis of water (the aquated electron and/or the hydrogen radical) and which, upon reduction, releases a sufficient amount of an effector of sufficient cytotoxic potency to kill tumour cells; and (b) irradiating said tumour cells to reduce the prodrug which is present at the locus of said tumour cells to release said cytotoxic effector.

The RACP can be of formula I

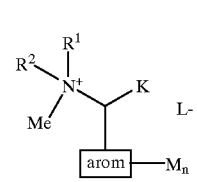

wherein $R^1$ represents H or $C_1$–$C_4$ alkyl optionally substituted with hydroxyl, ether, amino, methylamino or dimethylamino groups;

n is 0, 1 or 2, and each M is independently selected from $NO_2$, $CF_3$, $CH_2OR^1$, $COR^1$, $CONHR^1$, $OR^1$, $NR^1R^1$ and $SO_2R^1$ wherein $R^1$ is as defined above;

wherein arom is a single benzene ring or a 5- or 6-membered aromatic heterocycle containing one or two heteroatoms independently selected from O, S and N;

$L^-$ can be any pharmacologically acceptable counterion;

K is H or Me;

and wherein $R^2$ is represented by:

(i) a radical of formula II

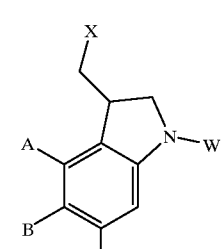

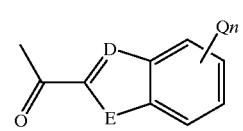

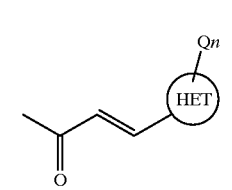

where X is halogen or $OSO_2R^1$ (where $R^1$ is as defined above);

A and b are each H or collectively represent an optionally substituted fused benzene or pyrrole ring system;

W is selected from $SO_2R^1$ (where $R^1$ is as defined above) and the structures IIa and IIb, where:

D is CH or N;

E is NH or O;

each Q is independently selected from $OR^1$ and $NR^1R^1$ wherein $R^1$ is as defined above;

n is 0, 1, 2 or 3; and

HET represents a 5- or 6-membered carbocycle or heterocycle containing one or two heteroatoms independently selected from O, S and N;

(ii) a radical of formula III

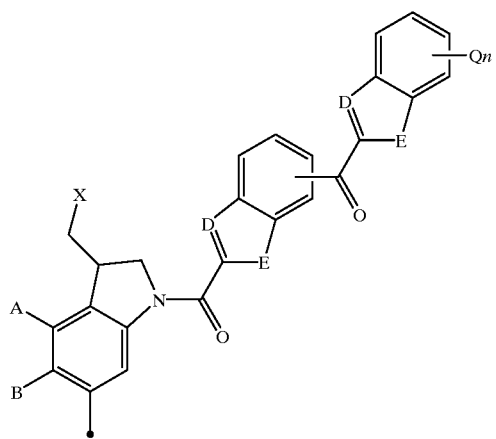

where X, A, B, Q and n are as defined above; and each D is independently CH or N; and each E is independently NH or O;

(iii) a radical of formula IV

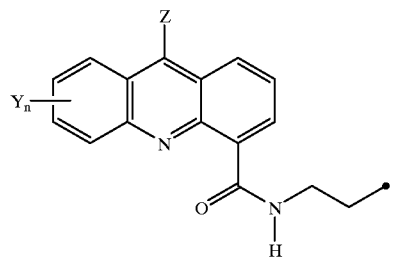

where Z is H or $NHR^1$ (where $R^1$ is as defined above);

n is 0, 1, 2 or 3; and each Y is independently selected from Me and OMe; or (iv) a radical of formula V

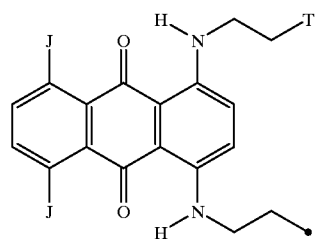

where each J is independently H or OH; and
T is $NMe_2$ or a moiety of the formula

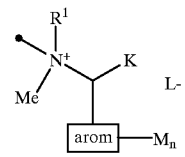

wherein n, M, arom, K and $R^1$ are as defined for formula I above.

A favoured subset of the compounds represented by formula I is represented by formula Ia

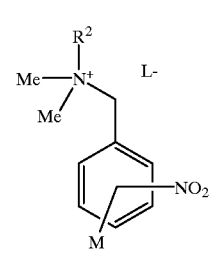

wherein $R^2$ and $L^-$ are defined as in formula I, and M is one of H, $CF_3$, $CH_2OR^1$, $COR^1$, $CONHR^1$, $OR^1$, $NR^1R^1$ or $SO_2R^1$ where $R^1$ represents H or $C_1$–$C_4$ alkyl optionally substituted with hydroxyl, ether, amino, methylamino or dimethyl-amino groups.

Alternatively, said RACP can be of formula VI

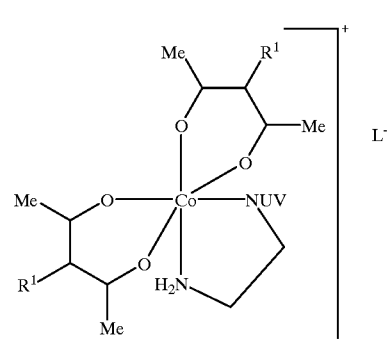

wherein each $R^1$ is independently as defined above;

U and V are both $CH_2CH_2Cl$, or U is H and V is a compound of formula II or formula III as defined above;

$L^-$ is any pharmaceutically acceptable anion.

In a further alternative, the RACP can be of formula VII

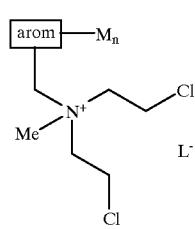

VII wherein M, n, arom and L– are defined as for formula I.

In a further alternative, the RACP can be of formula VIII

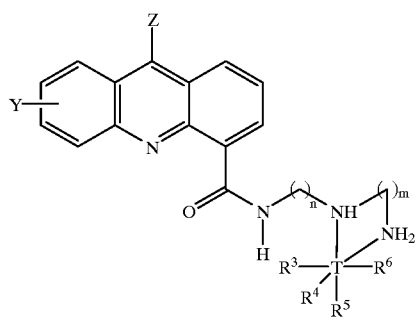

VIII wherein Y and Z are as defined for formula IV, T is Co(III) or Cr(III), n is from 2 to 6, m is 2 or 3, and $R^3$, $R^4$, $R^5$ and $R^6$ are each independently selected from CN, halogen, SCN, $H_2O$ and $NHR^1$ wherein $R^1$ is as defined above, or together represent 3-$R^7$acetonylacetonato (where $R^7$ is H, Me, $NO_2$, CN, SCN or SPh [where Ph is a benzene ring optionally substituted with up to two groups independently selected from Me, OMe, $NO_2$ and $NMe_2$]).

In all of the above definitions, where enantiomeric or diastereomeric forms are possible, all such possible forms are included.

In still a further aspect, the invention provides RACP compounds of general formula I as defined above.

In another aspect, the invention provides RACP compounds of general formula VIII as defined above.

In yet another aspect, the invention provides a pharmaceutical composition suitable for use in a method of treating neoplastic disease as defined above which includes a RACP compound of formula I, VI, VII or VIII and a pharmaceutically acceptable carrier or vehicle therefor.

In a final aspect, the present invention provides methods for preparing compounds of the general formulae I or VIII as defined above. Such methods are described below.

BRIEF DESCRIPTION OF THE DRAWINGS

While the invention is broadly as defined above, it will be appreciated by those persons skilled in the art that it also includes the specific embodiments described below. These specific embodiments are described in conjunction with the accompanying drawings in which.

DESCRIPTION OF THE INVENTION

Figure 1:
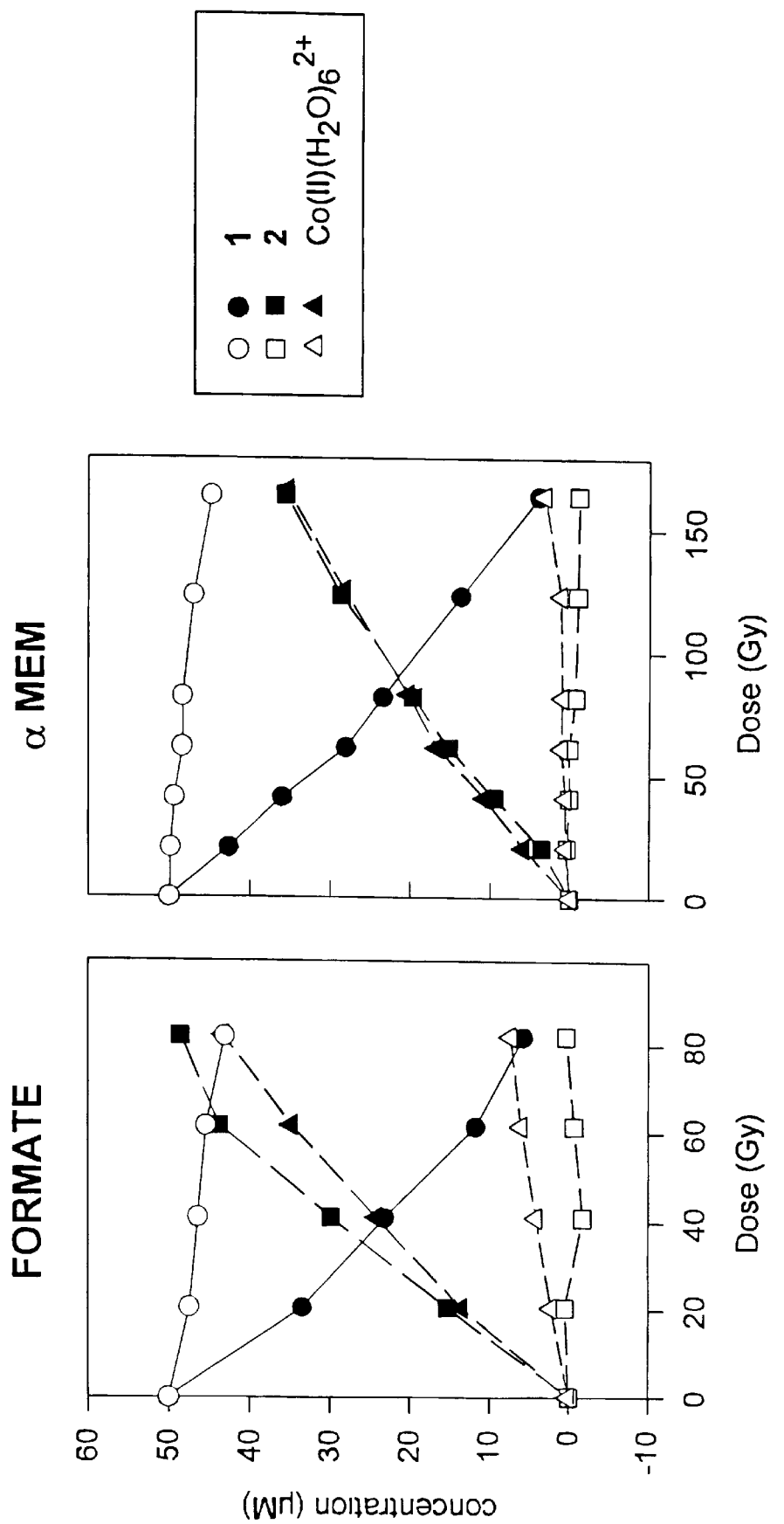
FIG. 1 shows the effect of radiolytic reduction of compound 1 (bis(3-methyl-2,4-pentanedionato)(N,N-bis(2-chloroethyl)ethylenediamine)cobalt (III) chloride) (50 µM) in sodium formate and in culture medium. Loss of compound 1 and formation of $Co(II)(H_2O)_6^{2+}$ and DCE (2) was determined by HPLC as described herein. The filled symbols represent deoxygenated solutions whereas the open symbols are equilibrated with air.

As defined above, this invention provides an approach to cancer therapy (radiation-activated cytotoxin therapy, RACT) in which ionising radiation is used to activate, by reduction, a RACP compound to form a more toxic species in a tumour. The mechanism of activation is believed to be as follows:

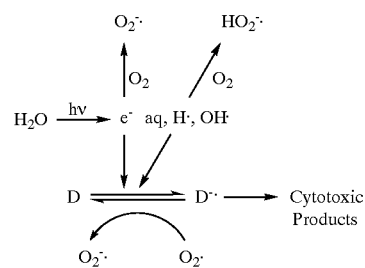

As can be seen, radiolysis of water generates three primary radical species (the aquated electron $e_{aq}^-$, the hydrogen radical H. and the hydroxyl radical OH.) of which $e_{aq}^-$ and H are strong reducing agents. These radiation-induced reductants are capable of reducing prodrugs of low reduction potential which are not substrates for enzymatic reduction and hence will not be activated outside the radiation field.

However, the yield of reducing species generated on the radiolysis of water is very low (corresponding to a total concentration of reductants equivalent to ca. 0.33 μmol/kg/ Gy). This places an upper limit on the amounts of activated cytotoxin which can be generated by this mechanism, although if the OH. gives rise secondarily to reducing radicals (e.g. via abstraction of H. from saturated carbon atoms) this may raise the theoretical upper limit towards the total radical yield of 0.62 μmol/kg/Gy.

Therefore, in order to be clinically effective in the present method of treatment of neoplastic disease while avoiding the disadvantages associated with BD therapy, the RACP compound must fulfill a number of general criteria. These criteria are that it exhibit low toxicity to the patient unless activated by irradiation; that it be able to be reduced by reducing agents generated by the radiolysis of water (the aquated electron and/or the hydrogen radical and/or secondary reducing radicals derived from OH.); and that it releases, upon reduction, a sufficient amount of an effector. A high cytotoxic potency of the effector is possibly the most important of the general requirements, as it helps to compensate for what might be a low yield of effector release.

In addition to these general criteria, it is preferred that the RACP compound satisfy the further requirement of not being an efficient substrate for enzymatic reduction.

Examples of prodrugs which fulfill at least the three general criteria are the compounds of formulae I, VI, VII and VIII as defined above. Of these compounds, those of formulae I and VIII are novel, whereas the compounds of formulae VI and VII are known.

The known compounds of formula VI and VII can be prepared by any of the methods described for their preparation in the literature. For example, the known compounds of formula VII can be prepared by reacting the free base of N,N-bis(2-chloroethyl)-ethylenediamine with trans-Na[Co (Me-acac)$_2$(NO$_2$)$_2$] (where Me-acac is 3-alkyl-pentane-2,4-dionato anion) in the presence of activated charcoal, followed by purification by cation-exchange chromatography [Ware, Palmer, Wilson and Denny, *J. Med. Chem.*, 36: 1839–1846, 1993].

As a further example, the known compounds of formula VII can be prepared by treatment of the appropriate nitrobenzyl chlorides with N-methyldiethanolamine in CH$_3$CN, followed by halogenation of the resulting quaternary diols with SOCl$_2$ at room temperature [Tercel, Wilson and Denny, *J. Med. Chem.* 36: 2578–2579, 1993; *J. Med. Chem.* 39: 1084–1094, 1996].

The novel compounds of the general formula I (in which $R^2$ is selected from formulae II–V) can be prepared by reacting the appropriate substituted halomethyl-substituted aromatic or heteroaromatic compounds directly with the appropriate tertiary aliphatic amines (for compounds of general formula I in which $R^2$ is of formulae IV and V), or by reacting the appropriate substituted aromatic or heteroaromatic aldehydes with the appropriate primary aliphatic amines, followed by reduction with sodium cyanoborohydride, and subsequent stepwise methylation, first with sodium cyanoborohydride/formaldehyde and then with an active methylating agent such as trimethyloxonium tetrafluoroborate (compounds of general formula I in which $R^2$ is of formulae II and III).

The method of Scheme 1 can be employed to prepare compounds of general formula I in which $R^2$ is of formulae II and III:

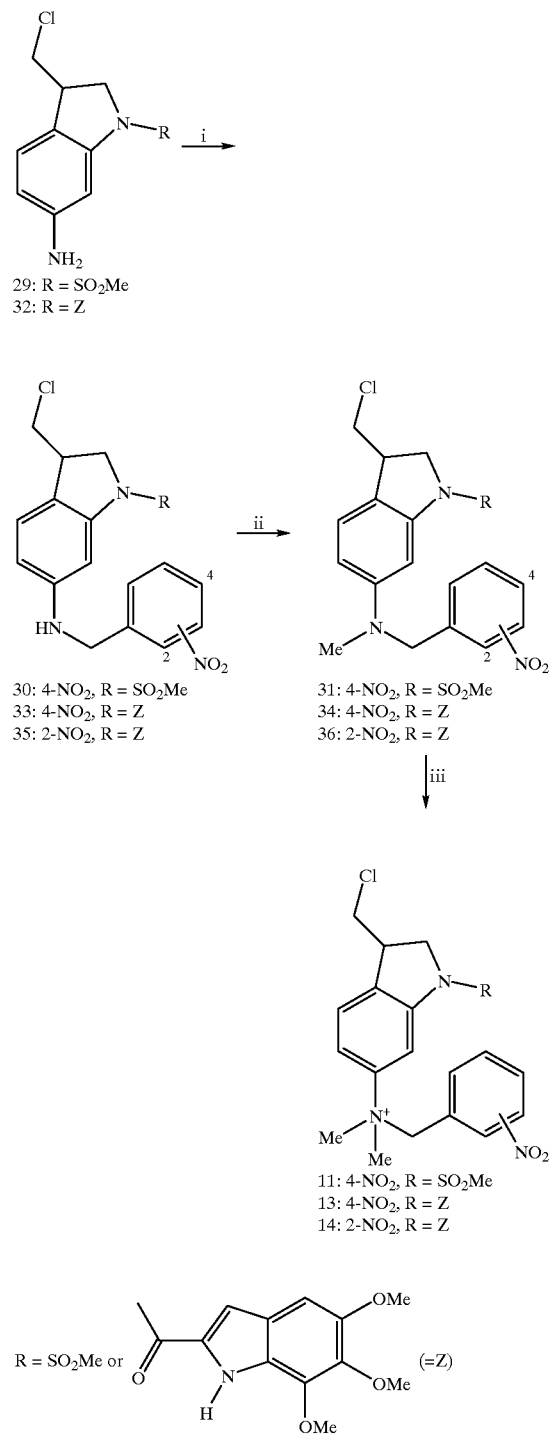

Scheme 1

29: R = SO$_2$Me
32: R = Z

30: 4-NO$_2$, R = SO$_2$Me
33: 4-NO$_2$, R = Z
35: 2-NO$_2$, R = Z

31: 4-NO$_2$, R = SO$_2$Me
34: 4-NO$_2$, R = Z
36: 2-NO$_2$, R = Z

11: 4-NO$_2$, R = SO$_2$Me
13: 4-NO$_2$, R = Z
14: 2-NO$_2$, R = Z

R = SO$_2$Me or (=Z)

i: 2- or 4-nitrobenzaldehye/TsOH/PhH/reflux,
   then NaBH$_3$CN/20° C./40 min.
ii: NaBH$_3$CN/HCHO/MeOH-THF/20° C./45 min.
iii: Me$_3$O$^+$BF$_4^-$/CH$_2$Cl$_2$/20° C./4 days, then ion
   exchange chromatography.

The typical method of Scheme 2 can be employed to prepare compounds of general formula I in which $R^2$ is of formula IV:

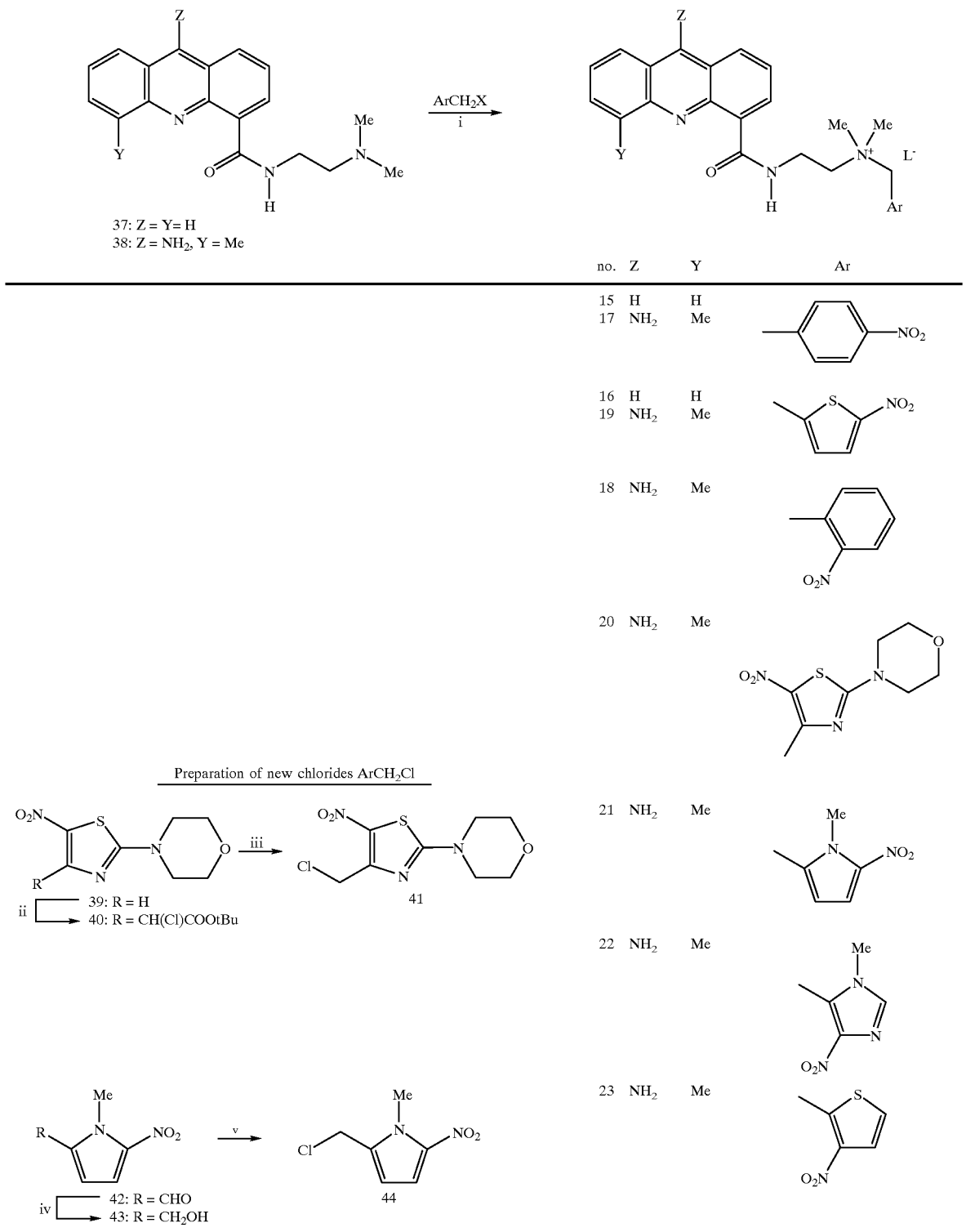
i: Benzene or MeCN/reflux/10–100 h.
ii: t-Butyl 2,2-dichloroacetate/KOtBu/DMF/10° C./1 h.
iii: AcOH/reflux/1.5 h.
iv: NaBH$_4$/MeOH/20° C./30 min.
v: MsCl/Et$_3$N/CH$_2$Cl$_2$/0° C./15 min.

The typical method of Scheme 3 can be employed to prepare compounds of general formula I in which $R^2$ is of formula V:

Scheme 3

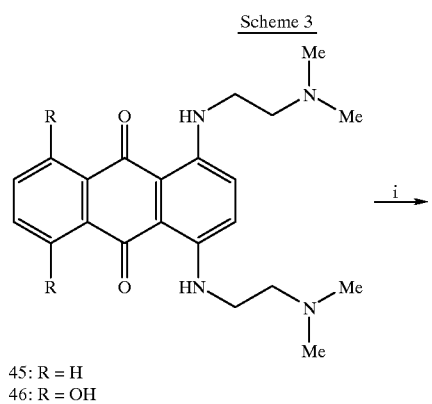

45: R = H
46: R = OH

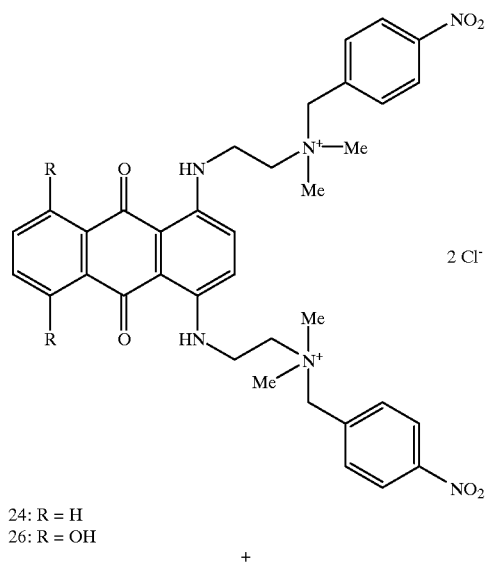

24: R = H
26: R = OH

+

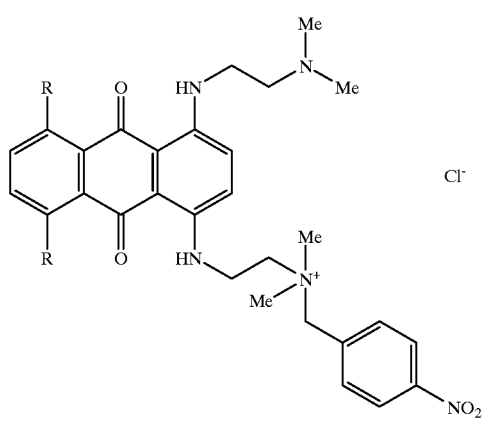

25: R = H
27: R = OH i: 4-nitrobenzyl chloride/MeCN/reflux/30 h.

The method of Scheme 4 can be employed generally to prepare the novel compounds of general formula VIII:

Scheme 4

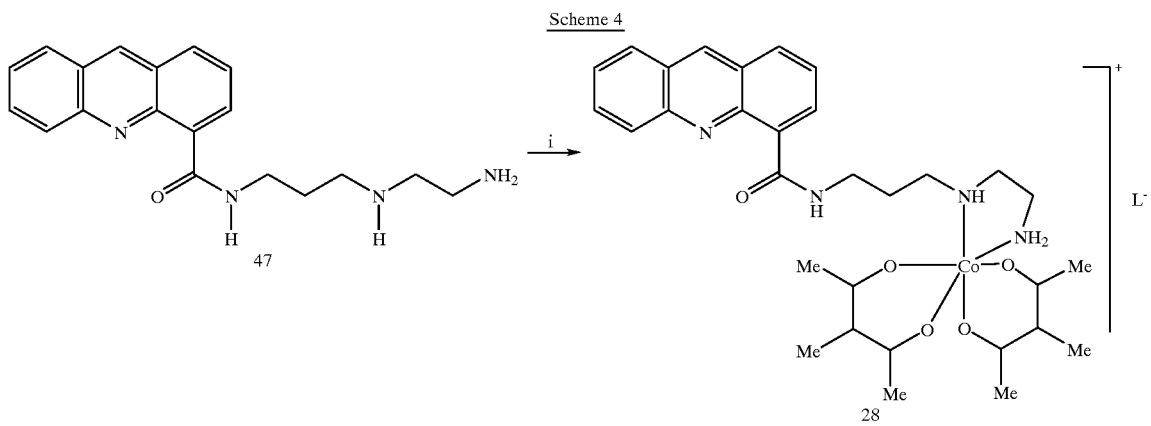

i: Co(Meacac)₃/charcoal/KOH/MeOH/20° C./2h

It will be appreciated that the starting material (shown as 47) in Scheme 4 can be varied depending on the desired values for Y, Z, n and m in the compound of formula VIII.

Similarly, Cr(Meacac)$_2$ [(OH)$_2$]$^+$ (prepared according to Abe, Y.; Shoji, M. *Inorg. Chem.* 1988, 27, 986) may be substituted for Co(Meacac)$_3$ as reagent, if a compound of formula VIII, in which T is Cr(III) is desired.

The RACP compounds for use in the therapeutic methods of the invention, whether compounds of formulae I, VI, VII or VIII, can be administered in any pharmaceutically appropriate form, such as orally administrable or injectable forms. Such forms can include conventional pharmaceutically acceptable vehicles, carriers or excipients.

In preferred embodiments of the invention, the RACP compounds are administered by injection. In this form of the invention, the administrable form of the RACP may comprise a sterile, reconstitutable, (lyophilised, water soluble) powder.

The clinical treatment schedule can be described as follows:

The RACP compounds would be administered to the patient at an appropriate dosage rate. The preferred dosage rate is expected to be in the range of about 0.01 to 100 mg/kg body weight of patient.

Any clinically-useful method of radiotherapy may be employed to activate the RACP in tumours. For example, conventional daily fractioned radiation (photons or electrons) may be used, in which case the tumour-bearing volume would be irradiated to a dose of about 2–2.5 Gy each day for a period of several weeks, to give a total dose in the order of 50 Gy. The RACP would be administered shortly before each radiation dose, at a timing such that the prodrug is at maximal concentration in the tumour at the time of irradiation.

It may be advantageous to use high dose rate radiation (achievable using electron beams) so that radiolytic consumption of oxygen is rapid enough to deplete residual oxygen in hypoxic regions, rendering these completely anoxic.

The present invention will now be described in relation to the following examples. It will however be understood by those persons skilled in the art that the examples given are illustrative only and are non-limiting.

EXAMPLE 1

Activation of a Cobalt(III)-nitrogen Mustard Complex of General Formula VI by Ionising Radiation The cobalt(III)-nitrogen mustard compound 1 (an example of general formula VI) is a bioreductive drug which is selectively toxic to hypoxic mammaliam cells in culture (Ware, D. C., Palmer, B. D., Wilson, W. R and Denny, W. A. *J. Med. Chem.*, 36, 1839–46, 1993; Wilson W. R, Moselen, J. W., Cliffe, S., Denny, W. A. and Ware, D. C. *Int. J. Radiat. Oncol. Biol. Phys.*, 29, 323–327, 1994). The proposed mechanism of bioreductive activation, involving one-electron reduction to the corresponding Co(II) compound and dissociation of the latter to release and thereby activate the coordinated nitrogen mustard ligand DCE (2), is as follows:

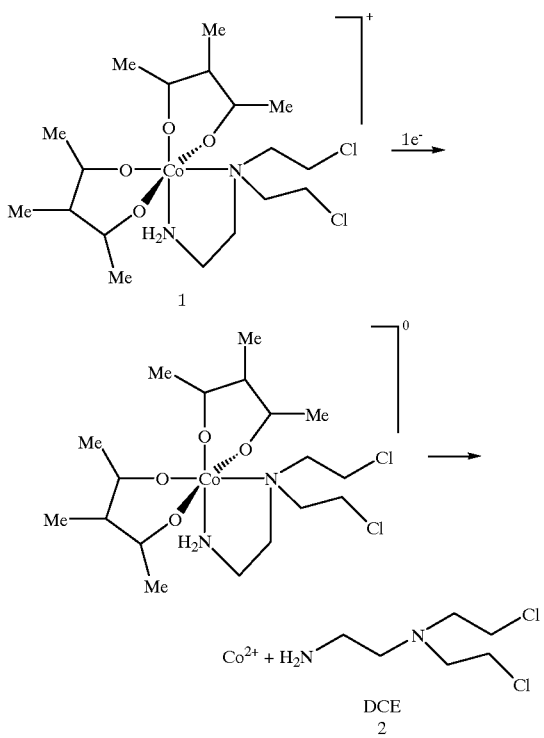

The present example shows that reductive activation of compound 1 can be effected using ionising radiation rather than a biological reducing system.

A solution of compound 1 (50 μM in 0.1M sodium formate, 0.085 M sodium hydrogen phosphate, adjusted to pH 7.0 with 8.5% orthophosphoric acid) was deaerated by evacuation and irradiated using a cobalt-60 source at a dose rate of 50 Gy/min. The products were analysed by HPLC after derivatisation with 4-(2-pyridylazo)resorcinol to detect Co(II)(H$_2$O)$_6^{2+}$, and after derivatisation with diethyldithiocarbamate (DDC) to detect DCE. The loss of the parent complex and the formation of Co(II)(H$_2$O)$_6^{2+}$ and DCE is shown as a function of radiation dose in FIG. 1.

The initial gradient of these curves corresponds to that expected for a one-electron reduction (yield of reductants in formate buffer=0.62 μmol.L$^{-1}$.Gy$^{-1}$; thus one-electron reduction would require a radiation dose of 81 Gy in this experiment). The consumption of compound I and formation of DCE (2) and Co(II)(H$_2$O)$_6^{2+}$ in this system is inhibited by oxygen (FIG. 1). Release of DCE (2) and Co(II)(H$_2$O)$_6^{2+}$ from compound 1 by irradiation was also observed in culture medium (αMEM)(FIG. 1).

Figure 2:
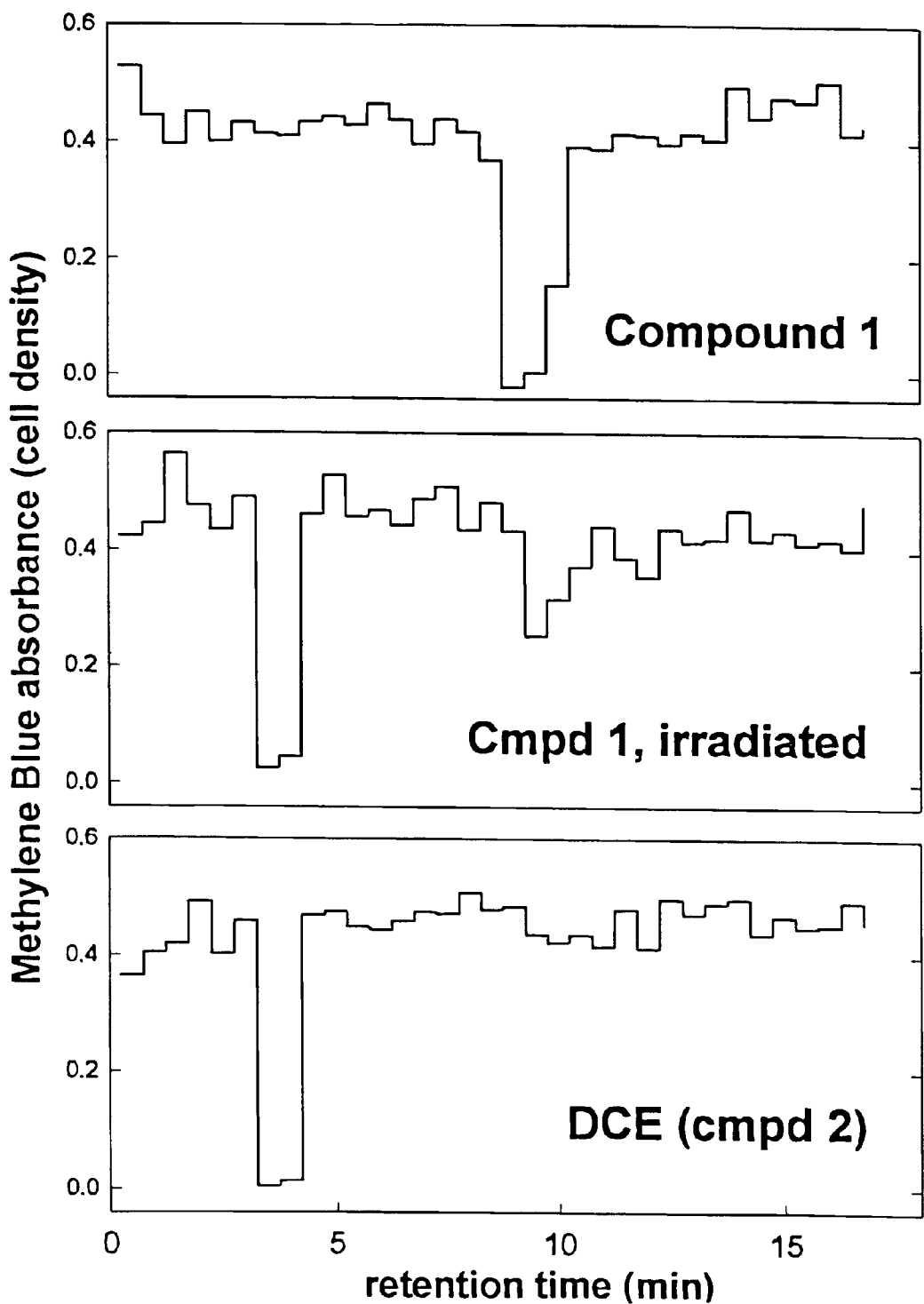
FIG. 2 shows the formation of DCE (2) by radiolysis of compound 1 in deoxygenated formate solution as demonstrated by HPLC/bioassay.

Bioassay experiments demonstrate that the cytotoxic activity in solutions of compound 1 is changed qualitatively and quantitatively by irradiation. A solution of compound 1 in sodium formate was irradiated to a dose corresponding to one reducing equivalent, and the products analysed by HPLC. The column eluate was bioassayed against log-phase UV4 cells growing in 96-well plates. The results show the loss of bioactivity in the region corresponding to the parent, and the appearance of a new peak of bioactivity corresponding in retention time to authentic DCE (FIG. 2).

EXAMPLE 2

Figure 4:
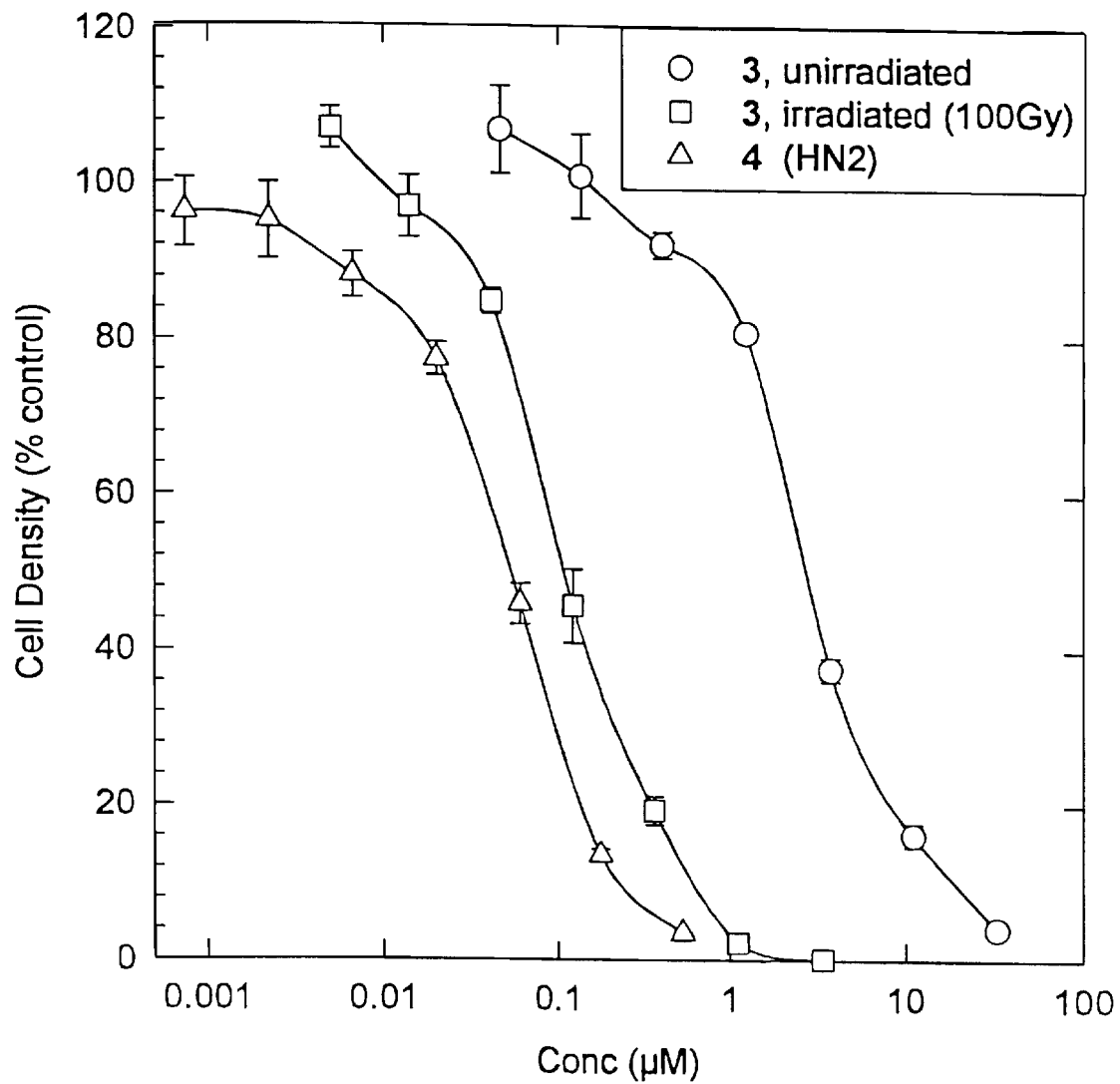
FIG. 4 shows the increase in cytotoxicity of a solution of 3 (100 µM in αMEM culture medium) after irrradiation under anoxic conditions at a dose of 100 Gy as demonstrated by bioassay against UV4 cells in 96 well plates as described herein. The cytotoxicity of authentic 4 (HN2) is also shown.

Activation of a (nitroimidazolyl)methyl Quaternary Ammonium Nitrogen Mustard Derivative of General Formula VII by Ionising Radiation The proposed mechanism of reductive activation of the (nitroimidazolyl)methyl quaternary ammonium nitrogen mustard (3) by ionising radiation, leading to release of mechlorethamine (4, HN2) as the cytotoxic species, is shown as follows:

The increase in cytotoxicity of solutions of 3 as a result of irradiation under anoxic conditions is demonstrated in FIG. 4. In this experiment a solution of 3 (200 μM in αMEM) was

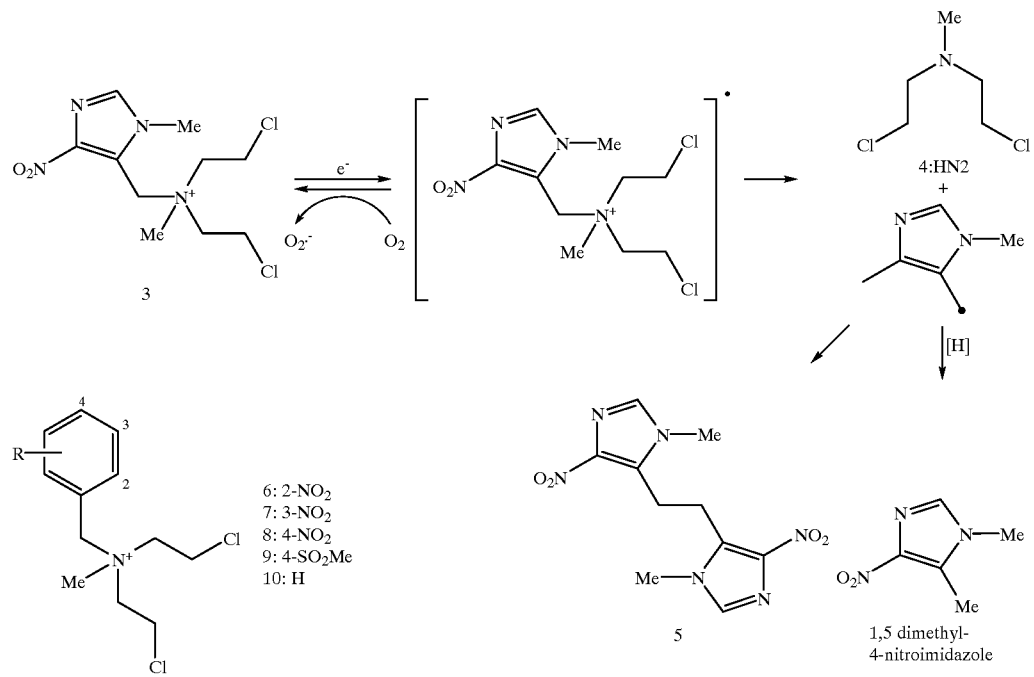

The formation of 1,5-dimethyl-4-nitroimidazole and the dimer 5, which were also identified and quantitated, are properly markers for the proposed one-electron reduction route.

Figure 3:
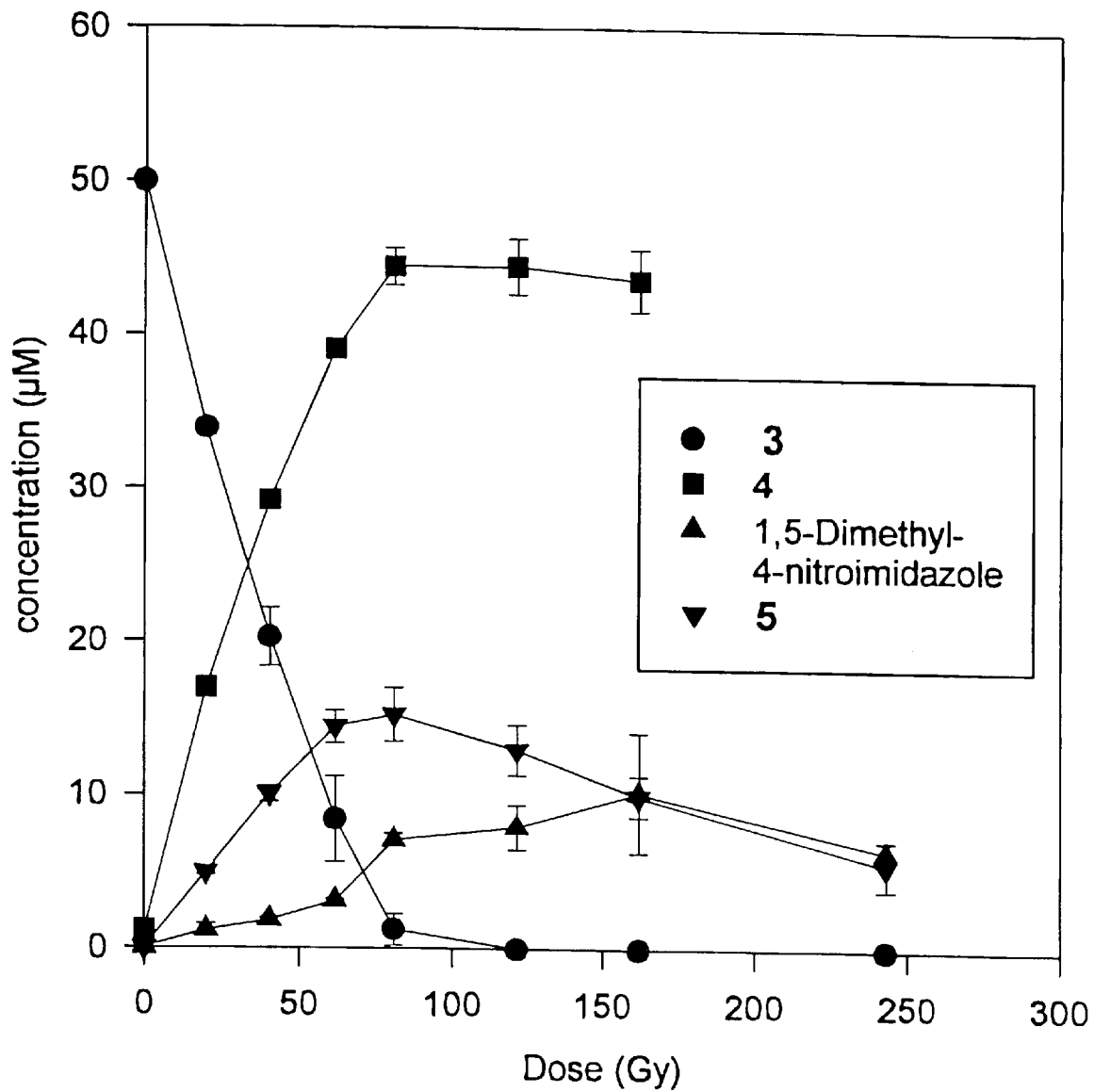
FIG. 3 shows the effect of radiolytic reduction of compound 3-(N,N-bis(2-chloroethyl)-N-methyl-N-[(1-methyl4-nitro-5-imidazolyl)methyl]ammonium chloride)) (50 µM) in sodium-formate. Loss of compound 3 and formation of the cytotoxic product 4 (HN2) was determined by HPLC as described herein.

A solution of compound 3 (50 μM in 0.1 M sodium formate/0.085 sodium hydrogen phosphate, pH 7.0) was irradiated at a range of doses using a cobalt-60 source (ca. 40 Gy/min) under anoxic conditions, incubated with diethyldithiocarbamate (DDC) to derivatise any HN2 released, and analysed by HPLC (FIG. 3; values are mean and error bars are ranges for two independent experiments). Loss of compound 3 was observed, with an initial G value of approximately 0.72 μM/Gy, corresponding to a stoichiometry of 1.16 mol prodrug reduced/mol radiolytic reductants generated. An adduct between (4;HN2) and DDC was detected, its identity being confirmed by comparison (retention time and spectrum) with the authentic synthetic DDC-HN2 diadduct. The initial G value for HN2 formation was 0.76 μM/Gy, and the maximum yield (at a radiation dose corresponding to one reducing equivalent) was 91% of the initial prodrug concentration. Two other products consistent with the above scheme (1,5-dimethyl-4-nitroimdazole and the dimer 5) were identified by comparison with authentic compounds. The total yield of methylimidazolyl radicals accounted for by these products (twice the yield of 5 plus the yield of 1,5-dimethyl-4-nitroimidazole) was 40.6 μM (81%). The observation that the stoichiometry of prodrug loss and HN2 formation is slightly greater than unity is suggestive of a short radical chain reaction such as reduction of methylimidazolyl radicals by formate to generate $CO_2^{.-}$ radicals and 1,5-dimethyl-4-nitroimidazole. This interpretation was supported by separate experiments in which 3 was reduced by radiation in 0.1 M butanol/water, which gave 4 and 5 in high yield while 1,5-dimethyl-4-nitroimidazole was present in only trace amounts.

deoxygenated by bubbling with 5% $CO_2$/95% $N_2$ and irradiated with 4 MeV electrons using a linear accelerator (100 Gy). The solution was then titrated against log-phase UV4 cells in 96-well plates. The cells were exposed to the irradiated solution for 4 hr under aerobic conditions ($CO_2$ incubator, 37° C.). The wells were then washed with fresh medium and the cells were cultured for a further 4 days before determining cell density by staining with methylene blue. The cytotoxicity of the irradiated solution (apparent $IC_{50}$ 0.11 μM, based on the concentration of 3 prior to irradiation) was intermediate between that of unirradiated 3 ($IC_{50}$ 3.0 μM) and that of authentic 4 ($IC_{50}$ 0.055 μM). The change in apparent $IC_{50}$ with radiation dose in experiments of this type, and comparison with $IC_{50}$ values of the prodrug and effector, is shown in FIG. 5A.

A method is described below for estimating, from the apparent $IC_{50}$, the concentration of cytotoxic effector in irradiated prodrug solutions. Using this method, the concentration of HN2 in irradiated solutions of 3 (100 μM in αMEM) was estimated from the $IC_{50}$ values shown in FIG. 5A. These calculations indicate an approximately linear increase in apparent HN2 concentration with dose (FIG. 5B), with a G value for release of effector (G(+E)) of 0.32 μM/Gy under anoxic conditions. Irradiation in the presence of oxygen (continuous bubbling with 5% $CO_2$/95% $O_2$ during irradiation) gave a G(+E) value of 0.013 μM/Gy, indicating effective inhibition by oxygen.

The nitrobenzyl quaternary ammonium nitrogen mustard analogues (6–10), (N,N-bis(2-chloroethyl-N-methyl-N-(2-nitrobenzyl)ammonium chloride, N,N-bis(2-chloroethyl-N-methyl-N-(3-nitrobenzyl)ammonium chloride, N,N-bis(2-chloroethyl-N-methyl-N-(4-nitrobenzyl)ammonium chloride, N,N-bis(2-chloroethyl-N-methyl-N-(4-methylsulfonyl)benzyl)ammnonium chloride, and N,N-bis(2-chloroethyl-N-methyl-N-benzylammonium chloride, respectively) some of which are known bioreductive drugs with selective toxicity for hypoxic cells in culture (Tercel, M., Wilson, W. R. and Denny, *J. Med. Chem.*, 36, 2578–2579, 1993; Denny, W. A., Wilson, W. R., Tercel, M., van Zijl, P. and Pullen, S. M. *Int. J. Radiat. Oncol. Biol. Phys.*, 29, 317–321, 1994), also release 4 on exposure to ionising radiation.

EXAMPLE 3

Demonstration of Radiolytic Release of Cytotoxic Effectors from a Variety of Compounds of Formulae I, VI, VII and VIII The above methods have been used to demonstrate release of cytotoxic effectors on irradiation of solutions of the compounds shown in Table 1. Two different assays were used.

Assay 1: Irradiation of the prodrug (50 μM) in formate buffer, with analysis of products by HPLC.

The prodrug, was dissolved in water (typically to approximately 2 mM) and the concentration determined by spectrophotometry. This stock solution was diluted to a final concentration of 50 μM in 0.1 M sodium formate, 0.085 M, $Na_2HPO_4$ (adjusted to pH 7.0 with 8.5% orthophosphoric acid). A sample of 5 or 10 ml was evacuated in a glass tube and irradiated with a gamma source (cobalt-60, dose rate 40–50 Gy/min) to a range of total doses (typically 20.25, 40.5, 60.75, 81, 162 and 243 Gy). Immediately after irradiation, air was introduced and the sample was analysed by HPLC. The aliphatic mustard effectors 2 (DCE) and 4 (HN2) were derivatised with diethyldithiocarbamate (DDC) prior to HPLC by adding DDC from a stock solution at 100 mM in water (prepared freshly) to give a final concentration of 2.5 mM. Samples were incubated at 37° C. for 30 min (4) or 90 min (2). In the case of 4, an equal vol MeOH was then added to redissolve the product. HPLC analysis used a Waters C18 μbondapak column (8×100 mm) with a mobile phase comprising suitable linear gradients of MeCN in 0.45 M ammonium formate, pH 4.5 (flow rate 1.8 ml/min). Detection was by diode array absorbance (Hewlett Packard 1040A). Authentic synthetic standards of each effector were used as the basis for identification (retention time and spectrum) and quantitation. The G value for formation of effector, G(+E), was calculated from the initial slope of the plot of effector concentration versus radiation dose. The effectors 12, 37 (DACA) and 46 (AMAC) were sufficiently stable to be detected directly by HPLC, without derivatisation. FIGS. 1 and 3 illustrate results of this assay.

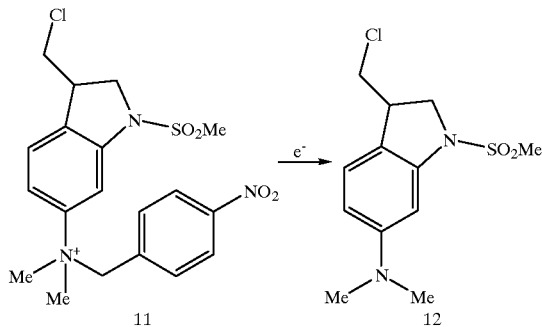

Assay 2: Irradiation of the prodrug in tissue culture medium (αMEM), with bioassay of the irradiated solution against UV4 cells.

A solution of prodrug was prepared in culture medium (αMEM), without use of organic solvents, and sterilised by filtration. The prodrug concentration in this solution was determined by spectrophotometry or HPLC. Samples (0.5 ml) in small glass test tubes were gassed vigorously (to cause turbulent mixing) with hurmidified 5% $CO_2$/95% $N_2$ or 5% $CO_2$/95% $O_2$ for 5 min (200 ml/min), using an 18 gauge needle through a rubber septum. Immediately after withdrawing the needle the sample was irradiated (4 MeV electrons, using a linear accelerator) to the required dose, using a charge collection plate (calibrated against the Fricke dosimeter) to determine the actual dose delivered. For experiments using 95% $O_2$, gassing was continued during irradiation to minimize radiolytic oxygen consumption. In most experiments the dose/pulse was approximately 3 Gy, and the pulse frequency was approximately 30 per min. Irradiated samples were transferred to cryogenic vials and frozen in liquid nitrogen within 45 seconds of the end of irradiation. These samples were stored at −80° C. until bioassay.

The bioassay was performed using log-phase cultures of UV4 cells in 96-well plates, seeded 24 hr previously (300 cells in 50 μl αMEM containing 5% foetal calf serum per well). The drug sample was thawed rapidly in a 37° C. waterbath, foetal calf serum added to a final concentration of 5%, diluted if necessary, and titrated across the 96-well plate using serial 2 or 3-fold dilutions in duplicate or triplicate. The elapsed time between thawing and titrating was <10 min. Plates were incubated at 37° C. for 4 hr under aerobic conditions (5% $CO_2$ incubator), the wells were washed three times with fresh medium and the cells grown for a further 4 days in 150 μl αMEM with 5% FCS. Cells were stained with methylene blue or suphorhodamine B, and absorbances determined with a plate reader. The $IC_{50}$ value was calculated as the drug concentration required to lower the absorbance to 50% of that of controls on the same plate. The $IC_{50}$ of irradiated solutions was expressed with respect to the starting concentration of the prodrug. (E.g. if the $IC_{50}$ of the unirradiated prodrug was 10 μM, and the apparent cytotoxicity was increased by a factor of 10 after irradiation, the resulting $IC_{50}$ was descnrbed as 1 μM).

The following controls were included in each bioassay experiment:

1. Prodrug freshly dissolved, or diluted from frozen stock solution, immediately before bioassay.
2. Unirradiated prodrug which had been gassed and processed (frozen and thawed) as for the irradiated samples.
3. Effector freshly dissolved, or diluted from a frozen stock solution in which it is known to be stable, immediately before bioassay.
4. Effector diluted into αMEM and immediately frozen in liquid $N_2$.

There was no consistent difference between controls 1 and 2, or 3 and 4, for any of the compounds tested indicating that there was no significant compound loss during freezing and thawing, and that there was no significant non-radiolytic activation in formate buffer.

The concentration of effector in the irradiated drug solutions, [E], was calculated from the apparent $IC_{50}$ of the irradiated mixture, $IC_{50}$,M (where the concentration is expressed with respect to the intitial concentration of prodrug) using the following relationship:

$$[E] = \frac{\left(\frac{IC_{50},E}{IC_{50},M} \times [P]_0\right) - \left(\frac{IC_{50},E}{IC_{50},P} \times [P]_0\right)}{1 - \frac{IC_{50},E}{IC_{50},P}}$$

where $IC_{50}$,E is the $IC_{50}$ value of the authentic effector
$IC_{50}$,P is the $IC_{50}$ of (unirradiated) prodrug
and $[P_o]$ is the initial concentration of the prodrug in the irradiated solution.

Figure 5:
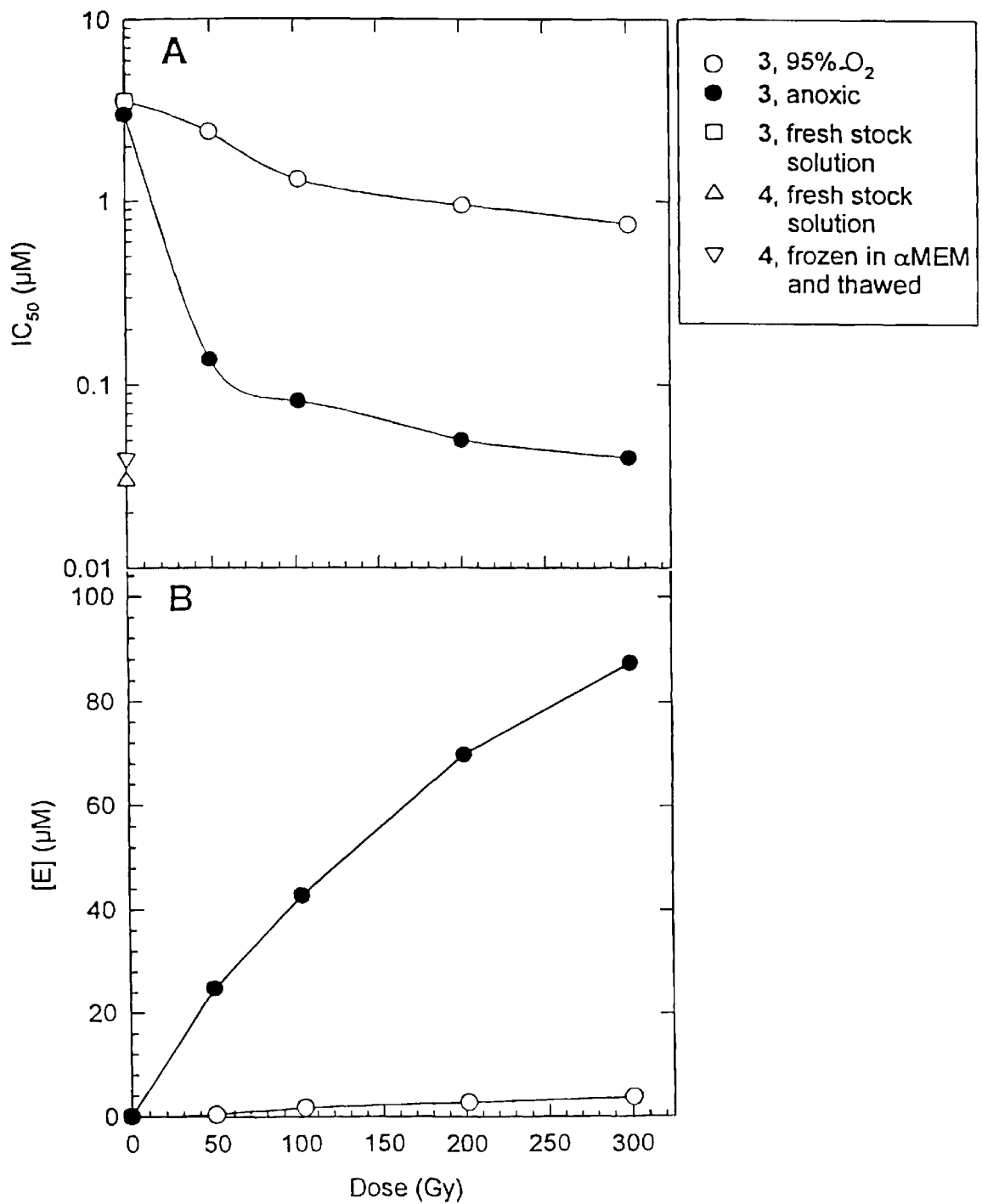
FIG. 5 shows the radiation dose dependence of the cytotoxicity of solutions of 3 (100 µM in αMEM), and the estimated concentrations of the released cytotoxic effector (4, HN2), under aerobic (open symbols) or anoxic (filled symbols) conditions. Concentration of 4 in the irradiated solutions were calculated using the method described herein.

The derivation of the above relationship makes the assumption that the cytotoxicity of the effector is not modified by the prodrug, and that when the toxicity of the prodrug itself is significant (as will be the case at low radiation doses when only a small percentage conversion of prodrug to effector has occurred) then the combined toxicity is additive. In particular, we assume that the prodrug concentration can be expressed as an equivalent concentration of effector. The above equation also assumes that the stoichiometry of effector formation (mol effector formed/mol prodrug reduced) is unity. FIG. 5 demonstrates the use of the above equation to estimate effector yields.

Interpretation of Assays

The above assays give different information. Assay 1 establishes whether the intended effector is released from the prodrug when the latter is reduced by radiation. Assay 2 examines to what extent the cytotoxicity of the prodrug solution is increased following irradiation. This will depend on the efficiency of effector release from the reduced prodrug (as measured by Assay 1), but also on the efficiency of prodrug reduction by radiation in the presence of scavenging species in culture medium, and on the difference in cytotoxic potency between the prodrug and effector.

In assay 2, the concentration of cytotoxic effector in irradiated solutions can be calculated from the measured $IC_{50}$ of the solution, provided that certain assumptions are met (see above), and the G value for release of effector (G(+E); can therefore be calculated. However, it should be noted that even if the efficiency of prodrug reduction is undiminished by competing electron acceptors in medium, the G value is expected to be lower in medium than in formate where oxidising OH. radicals are quantitatively converted to reducing $CO_2.^-$ radicals. Since OH represents approximately half the primary radical yield in water, the theoretical yield of radiolytcally-generated reductants in medium is approximately half that in formate (unless OH. gives rise to reducing radicals on reaction with constituents in medium).

In identifying preferred RACP, we seek compounds with high values of G(+E) and low values of $IC_{50}$,E. Ideally, radiolytic activation of the prodrug, using a clinially relevant radiation dose of 2 Gy, should provide an effector concentration which is large relative to $IC_{50}$,E. We thus evaluate the ratio $R_2$ where $R_2 = [E]_2/(IC_{50},E)$ and $[E]_2$ is the effector concentration at 2 Gy, calculated from G(+E).

We note that G(+E) is not likely to be independent of prodrug concentration when scavengers are present since the ability of the prodrug to capture reducing equivalents competitively is then expected to increase with prodrug concentration. Thus if two prodrugs release the same effector, by the same mechanism, but have different $IC_{50}$ values (without irradiation), the less toxic analogue would allow use of higher prodrug concentrations in a biological system and would be expected to provide a higher G(+E) in cells as well as a higher prodrug/effector toxicity differential. Thus, in addition to seeking prodrugs with high values of $R_2$, we also seek prodrugs with high values of $IC_{50}$,P.

Results

The results for the above two assays are summarised in Table 1. $IC_{50}$ values for prodrugs and effectors were determined against the UV4 and SKOV3 cell lines. The UV4 cell line is hypersensitive to DNA alkylating agents (Hoy et al., *Mutation Research*, 130: 321–332, (1984)), while the SKOV3 cell line (derived from a human ovarian carcinoma) is considered more representative in its sensitivity. The most important screening parameters are therefore $IC_{50}$,P and $R_2$ for the SKOV3 cell line.

TABLE 1

Reductive activation of prodrugs by radiation: summary of yields of effectors, and cytotoxicity data for prodrugs and effectors.

| | | G(+E)[c], anoxic, µM/Gy | | UV4 | | | SKOV3 | | |
| --- | --- | --- | --- | --- | --- | --- | --- | --- | --- |
| | | Assay | | $IC_{50}$, P[f] | $IC_{50}$, E[g] | | | | |
| Cmpd | Effector[a] | 1[d] | Assay 2[e] | (µM) | (µM) | $R_2$[h] | $IC_{50}$, P(µM) | $IC_{50}$, E(µM) | $R_2$ |
| 11 | 12[b] | 0.38[i] | | 1135 ± 122 | 15 ± 6 | | | | |
| 15 | 37: DACA[b] | 0.072 | 0.067(150) | >150 | 0.49 ± 0.11 | 0.27 | >150 | 3.4 ± 0.8 | 0.039 |
| 16 | 37[b] | 0.19 | 0.13(167) | 40 ± 8 | 0.49 ± 0.11 | 0.53 | 169 ± 58 | 3.4 ± 0.8 | 0.076 |
| 17 | 38:AMAC[b] | 0.034 | 0.03 ± 0.01(5) | 0.78 ± 0.09 | 0.011 ± .001 | 5.5 | 4.0 ± 0.1 | 0.046 ± .002 | 1.3 |
| 18 | 38 | | 0.0025(15) | 3.1 ± 0.7 | 0.011 ± .001 | 0.45 | | | |
| 19 | 38 | | 0.020(15) | 0.16 ± 0.03 | 0.011 ± .001 | 3.6 | | | |
| 21 | 38 | | 0.04(15) | 2.0 ± 0.4 | 0.011 ± .001 | 7.3 | | | |
| 20 | 38 | | 0.006(15) | 1.0 ± 0.3 | 0.011 ± .001 | 1.1 | | | |
| 22 | 38 | | 0.06(15) | 1.9 ± 0.4 | 0.011 ± .001 | 11 | | | |
| 27 | 46:AQ4 | | 0.0056 ± 0.0008(1.6) | 0.27 ± 0.04 | 0.0021 ± 0.007 | 5.3 | 9.7 ± 0.03 | 0.074 ± 0.0004 | 0.15 |
| 1 | 2:DCE[b] | 0.76 | 0.15(50) | 0.30 ± 0.1 | 0.036 ± .004 | 8.3 | 20 ± 7 | 2.4 ± 0.3 | 0.12 |
| 28 | 47:DACA-EN[b] | 0.8 | | 31 ± 10 | 1.6 ± 0.4 | | 74 ± 17 | 1.6 ± 0.3 | |

TABLE 1-continued

Reductive activation of prodrugs by radiation: summary of yields of effectors, and cytotoxicity data for prodrugs and effectors.

| | | G(+E)[c], anoxic, µM/Gy | | UV4 | | | SKOV3 | | |
|---|---|---|---|---|---|---|---|---|---|
| | | Assay | | $IC_{50}$, P[f] | $IC_{50}$, E[g] | | | | |
| Cmpd | Effector[a] | 1[d] | Assay 2[e] | (µM) | (µM) | $R_2$[h] | $IC_{50}$, P(µM) | $IC_{50}$, E(µM) | $R_2$ |
| 6 | 4:HN2[b] | 0.26 | 0.114 ± .018 (200) | 61 ± 14 | 0.034 ± .008 | 6.7 | 10,080 ± 3600 | 1.09 ± .04 | 0.21 |
| 7 | 4[b] | 0.045 | | | | | | | |
| 8 | 4[b] | 0.20 | 0.04(150) | 35 | 0.034 ± .008 | 2.4 | | | |
| 9 | 4[b] | 0.19 | 0.068(400) | | | | | | |
| 10 | 4[b] | 0.05 | | | | | | | |
| 3 | 4[b] | 0.74, 0.76 | 0.26(20) 0.34(100) 0.43 ± 0.03 (200) | 1.6 ± 0.3 | 0.034 ± .008 | 15 20 25 | 143 ± 25 | 1.09 ± .04 | 0.48 0.62 0.79 |

Footnotes:
[a]Structural formulae shown in FIGS. 1–3 and Schemes 1–4.
[b]The identity of the indicated effector was confirmed as a product of radiolysis in formate buffer (assay I) by comparison of HPLC retention time and absorbance spectrum with that of authentic (synthetic) standard
[c]Yield of effector
[d]Assay 1: Radiolytic reduction in sodium formate, with analysis of effector formation by HPLC. See text for details. Where two values are shown, these are from independent experiments
[e]Assay 2: Radiolytic reduction in αMEM, with effector formation estimated by bioassay against UV4 cells. See text for details. When errors are shown, the values are the mean and sem for independent experiments. (Repeat bioassay of the same irradiated solution does not count as a separate experiment). Values in parenthesis are the concentration of prodrug in the irradiated solution.
[f]$IC_{50}$ of the unirradiated prodrug against the indicated cell line. 4 hr drug exposure under aerobic conditions. Values are mean ± SEM for independent experiments.
[g]$IC_{50}$ of the authentic effector (identified in column 2) against the indicated cell line. 4 hr drug exposure under aerobic conditions. Values are mean ± SEM for independent experiments.
[h][E]$_2$/($IC_{50}$, E), where [E]$_2$ is the effector concentration at 2 Gy, calculated from G(+E) in αMEM (assay 2)
[i]Irradiated at one dose only (81 Gy).

EXAMPLE 4a

Preparation of 3-(chloromethyl)-6-[N,N-dimethyl-N-(4-nitrobenzyl)-ammonio]-1-[(5',6',7'-trimethoxyindol-2'-yl)carbonyl]indoline chloride (compound 13) of General Formula I by the Method Outlined in Scheme 1

A mixture of 6-amino-3-(chloromethyl)-1-[(5',6',7'-trimethoxyindol-2'-yl)carbonyl]-indoline (32) [for preparation, see Example 8] (464 mg, 1.12 mmol), 4-nitrobenzaldehyde (202 mg, 1.34 mmol) and toluenesulfonic acid monohydrate (21 mg, 0.1 mmol) in benzene (30 mL) was heated to reflux and most of the benzene distilled off over 15 min. The remaining mixture was evaporated to dryness and the residue dissolved in THF (30 mL) and MeOH (10 mL). Sodium cyanoborohydride (0.14 g, 2.23 mmol) then 2 N HCl (0.3 mL) were added and the mixture stirred at 20° C. for 25 min, then evaporated. The residue was diluted with aq. NaCl, extracted with EtOAc (×2), and the extracts were dried ($Na_2SO_4$) and evaporated. Dry column chromatography, eluting with EtOAc/petroleum ether (2:3), gave, 3-(chloromethyl)-6-[N-(4-nitrobenzyl) amino]-1-[(5',6',7'-trimethoxyindol-2'-yl)carbonyl]indoline (33) as a yellow-orange oil (545 mg, 89%). $^1$H NMR (CDCl$_3$) δ 9.56 (s, 1 H, indole NH), 8.15 (d, J=8.7 Hz, 2 H, ArH o to NO$_2$), 7.77 (d, J=1.8 Hz, 1 H, H-7), 7.50 (d, J=8.7 Hz, 2 H, ArH m to NO$_2$), 7.02 (d, J=8.2 Hz, 1 H, H-4), 6.94 (d, J=2.4 Hz, 1 H, H-3'), 6.85 (s, 1 H, H-4'), 6.26 (dd, J=8.2, 2.2 Hz, 1 H, H-5), 4.63–4.56 (m, 1 H, H-2), 4.48 (s, 2 H, NCH$_2$Ar), 4.42 (dd, J=10.8, 4.2 Hz, 1 H, H-2), 4.05 (s, 3 H, OCH$_3$), 3.93 (s, 3 H, OCH$_3$), 3.90 (s, 3 H, OCH$_3$), 3.78–3.69 (m, 2 H, CHCH$_2$Cl), 3.54–3.46 (m, 1 H, CHCH$_2$Cl); $^{13}$C NMR δ 160.3 (CO), 150.1, 148.3, 147.2, 147.1, 144.8, 140.5, 138.8, 129.9, 125.5, 123.6, 120.6 (aromatic C), 127.7, 123.8 (o,m to NO$_2$), 124.7, 108.5, 106.4, 103.1, 97.6 (C-4,5,7,3',4'), 61.5, 61.1, 56.2 (3×OCH$_3$), 54.8 (C-2), 47.5, 47.3 (CH$_2$Cl, NCH$_2$Ar), 43.1 (C-3). MS (DEI, $^{35}$Cl) m/z 550 (50%, M$^+$), 234 (100%); HRMS (FAB) calcd. for C$_{28}$H$_{27}$ClN$_4$O$_6$ (M+H) 551.1697, found 551.1690.

Sodium cyanoborohydride (0.12 g, 1.9 mmol) then 2 N HCl (1.0 mL) were added to a solution of the above indoline (33) (545 mg, 0.96 mmol) and formaldehyde (0.87 mL of a 40% w/v aq. solution, 12 mmol) in THF (20 mL) and MeOH (15 mL) and the mixture stirred at 20° C. for 50 min. The mixture was diluted with aq. NaHCO$_3$, extracted with EtOAc (×2), and the extracts dried (Na$_2$SO$_4$) and evaporated. Dry column chromatography on silica gel, eluting with EtOAc/petroleum ether (2:3), gave 3-(chloromethyl)-6-[N-methyl-N-(4-nitrobenzyl)amino]-1-[(5',6',7'-trimethoxyindol-2'-yl)carbonyl]indoline (34) as a yellow-orange oil (348 mg, 62%).

A sample was crystallised from EtOAc-Et$_2$O as yellow needles, mp 178–179° C. $^1$H NMR (CDCl$_3$) δ 9.46 (s, 1 H, indole NH), 8.16 (d, J=8.7 Hz, 2 H, ArH o to NO$_2$), 7.88 (d, J=1.7 Hz, 1 H, H-7), 7.39 (d, J=8.7 Hz, 2 H, ArH m to NO$_2$), 7.09 (d, J=8.4 Hz, 1 H, H-4), 6.95 (d, J=2.3 Hz, 1 H, H-3'), 6.86 (s, 1 H, H-4'), 6.41 (dd, J=8.4, 2.5 Hz, 1 H, H-5), 4.66 (s, 2 H, NCH$_2$Ar), 4.61 (dd, J=10.8, 8.7 Hz, 1 H, H-2), 4.44 (dd, J=10.8, 4.2 Hz, 1 H, H-2), 4.04 (s, 3 H, OCH$_3$), 3.93 (s, 3 H, OCH$_3$), 3.90 (s, 3 H, OCH$_3$), 3.81–3.72 (m, 2 H, CHCH$_2$Cl), 3.56–3.48 (m, 1 H, CHCH$_2$Cl), 3.11 (s, 3 H, NCH$_3$); $^{13}$C NMR δ 160.3 (CO), 150.1, 150.0, 147.1, 146.8, 145.0, 140.5, 138.8, 129.9, 125.5, 123.6, 119.8 (aromatic C), 127.4, 123.9 (o,m to NO$_2$), 124.6, 108.4, 106.5, 102.4, 97.6 (C-4,5,7,3',4'), 61.5, 61.1, 56.3 (3×OCH$_3$), 56.6 (NCH$_2$Ar), 54.9 (C-2), 47.3 (CH$_2$Cl), 43.0 (C-3), 39.3 (NCH$_3$). Anal.

Calculated for $C_{29}H_{29}ClN_4O_6$: C, 61.7; H, 5.2; N, 9.9. Found: C, 61.9; H, 5.4; N, 9.8%.

Methyl trifluoromethanesulfonate (0.21 mL, 1.9 mmol) and 2,6-di-t-butylpyridine (0.42 mL, 1.9 mmol) were added to a solution of the above indoline (34) (352 mg, 0.62 mmol) in dry $CH_2Cl_2$ (6 mL) and the mixture allowed to stand at 20° C. for 3 days, then evaporated. The residue was dissolved in $CH_2Cl_2$, washed with water (×2), dried ($Na_2SO_4$), and evaporated. Trituration with $Et_2O$ (×5) removed all of the remaiing di-t-butylpyridine. The resulting pale yellow powder was dissolved in MeOH (5 mL) and water (2.5 mL) and passed through a column of Biorad AG 1-X4 ion exchange resin in the chloride form (10 g), eluting with MeOH-$H_2O$ (2:1, 20 mL). The eluate was evaporated, the residue dissolved in $CH_2Cl_2$, dried ($Na_2SO_4$), and evaporated. Trituration with EtOAc-$Et_2O$ then EtOAc-$CH_2Cl_2$ gave 3-(chloromethyl)-6-[N,N-dimethyl-N-(4-nitroberzyl)-ammonio]-1-[(5',6',7'-trimethoxyindol-2'-yl)carbonyl] indoline chloride (compound 13) as a pale yellow solid (126 mg, 33%), mp 124–125° C. $^1$H NMR [$(CD_3)_2SO$] δ 11.56 (d, J=1.7 Hz, 1 H, indole NH), 8.53 (s, 1 H, H-7), 8.20 (d, J=8.8 Hz, 2 H, ArH o to $NO_2$), 7.70 (s, 2 H, H-4,5), 7.48 (d, J=8.8 Hz, 2 H, ArH m to $NO_2$), 7.12 (d, J=2.1 Hz, 1 H, H-3'), 6.96 (s, 1 H, H-4'), 5.29 (s, 2 H, $NCH_2Ar$), 4.82–4.74 (m, 1 H, H-2), 4.41 (dd, J=10.8, 4.4 Hz, 1 H, H-2), 4.12–4.02 (m, 3 H, $CHCH_2Cl$), 3.92 (s, 3 H, $OCH_3$), 3.82 (s, 3 H, $OCH_3$), 3.79 (s, 3 H, $OCH_3$), 3.68 (s, 6 H, $NMe_2$); $^{13}$C NMR δ 160.6 (CO), 149.2, 148.4, 145.0, 144.2, 140.2, 139.0, 135.1, 134.5, 130.0, 129.9, 123.1 (aromatic C), 134.0, 123.4 (o,m to $NO_2$), 125.7, 117.2, 109.7, 106.9, 98.0 (C-4,5,7,3',4'), 70.1 ($NCH_2Ar$), 61.0, 60.9, 55.9 (3×$OCH_3$), 54.3 (C-2), 53.1, 52.8 ($NMe_2$), 47.3 ($CH_2Cl$), 41.5 (C-3). Anal. Calculated for $C_{30}H_{32}Cl_2N_4O_6.H_2O$: C, 56.9; H, 5.4; N, 8.8. Found: C, 57.2; H, 5.4; N, 8.9%.

EXAMPLE 4b

Preparation of 3-(chloromethyl)-6-[N,N-dimethyl-N-(2-nitrobenzyl)-ammonio]-1-[(5',6',7'-trimethoxyindol-2'-yl)carbonyl]indoline chloride (compound 14) of General Formula I by the Method Outlined in Scheme 1

Similar reaction of (32) and 2-nitrobenzaldehyde gave 3-(chloromethyl)-6-[N-(2-nitrobenzyl)amino]-1-[(5',6',7'-trimethoxyindol-2'-yl)carbonyl]indoline (35) as a yellow oil (72%). $^1$H NMR (CDCl$_3$) δ 9.45 (s, 1 H, indole NH), 8.07 (dd, J=8.2, 1.2 Hz, 1 H, ArH o to $NO_2$), 7.78 (d, J=1.8 Hz, 1 H, H-7), 7.68 (dd, J=7.7, 0.9 Hz, 1 H, ArH), 7.57 (td, J=7.5, 1.3 Hz, 1 H, ArH), 7.41 (td, J=7.7, 1.4 Hz, 1 H, ArH), 7.00 (d, J=8.3 Hz, 1 H, H-4), 6.94 (d, J=2.4 Hz, 1 H, H-3'), 6.85 (s, 1 H, H-4'), 6.23 (dd, J=8.3, 2.2 Hz, 1 H, H-5), 4.75 (s, 2 H, $NCH_2Ar$), 4.62–4.55 (m, 1 H, H-2), 4.42 (dd, J=10.7, 4.2 Hz, 1 H, H-2), 4.07 (s, 3 H, $OCH_3$), 3.94 (s, 3 H, $OCH_3$), 3.90 (s, 3 H, $OCH_3$), 3.78–3.68 (m, 2 H, $CHCH_2Cl$), 3.53–3.44 (m, 1 H, $CHCH_2Cl$); $^{13}$C NMR δ 160.2 (CO), 150.1, 148.4, 148.2, 144.8, 140.5, 138.8, 135.4, 129.9, 125.4, 123.6, 120.5 (aromatic C), 133.7, 130.0, 128.1, 125.2, 124.7, 108.3, 106.4, 103.1, 97.6 (aromatic CH), 61.5, 61.1, 56.3 (3×$OCH_3$), 54.8 (C-2), 47.3 ($CH_2Cl$), 45.8 ($NCH_2Ar$), 43.1 (C-3). MS (DEI, $^{35}$Cl) m/z 550 (50%, M$^+$), 234 (100%); HRMS (FAB) calcd. for $C_{28}H_{27}ClN_4O_6$ (M+H) 551.1697, found 551.1690.

Reaction of the above indoline (35) with sodium cyanoborohydride and formaldehyde as above gave 3-(chloromethyl)-6-[N-methyl-N-(2-nitrobenzyl)amino]-1-[(5',6',7'-trimethoxyindol-2'-yl)carbonyl]indoline (36) as an orange oil (72%). $^1$H NMR (CDCl$_3$) δ 9.41 (s, 1 H, indole NH), 8.14 (dd, J=8.1, 1.2 Hz, 1 H, ArH o to $NO_2$), 7.88 (d, J=2.0 Hz, 1 H, H-7), 7.56 (td, J=7.5, 1.2 Hz, 1 H, ArH p to $NO_2$), 7.45–7.67 (m, 2 H, ArH), 7.06 (d, J=8.4 Hz, 1 H, H-4), 6.95 (d, J=2.3 Hz, 1 H, H-3'), 6.86 (s, 1 H, H-4'), 6.32 (dd, J=8.4, 2.5 Hz, 1 H, H-5), 4.95 (s, 2 H, $NCH_2Ar$), 4.61 (dd, J=10.8, 8.7 Hz, 1 H, H-2), 4.44 (dd, J=10.8, 4.2 Hz, 1 H, H-2), 4.05 (s, 3 H, $OCH_3$), 3.93 (s, 3 H, $OCH_3$), 3.90 (s, 3 H, $OCH_3$), 3.80–3.72 (m, 2 H, $CHCH_2Cl$), 3.55–3.47 (m, 1 H, $CHCH_2Cl$), 3.12 (s, 3 H, $NCH_3$); $^{13}$C NMR δ 165.8 (CO), 150.1, 150.0, 148.1, 145.0, 141.0, 140.5, 138.8, 135.1, 129.9, 123.6, 119.5 (aromatic C), 133.9, 128.5, 127.8, 125.5, 124.6, 108.1, 106.4, 101.9, 97.6 (aromatic CH), 61.5, 61.1, 56.3 (3×$OCH_3$), 55.2, 54.9 ($NCH_2Ar$, C-2), 47.3 ($CH_2Cl$), 43.1 (C-3), 39.1 ($NCH_3$). MS (DEI, $^{35}$Cl) m/z 564 (30%, M$^+$), 429 (60%, M– $C_7H_5NO_2$), 234 (100%); HRMS calcd. for $C_{29}H_{29}ClN_4O_6$ 564.17756, found 564.17897.

Reaction of the above indoline (36) with methyl trifluoromethanesulfonate and 2,6-di-t-butylpyridine as above, and ion exchange chromatography, followed by trituration with hot $CH_2Cl_2$, gave 3-(chloromethyl)-6-[N,N-dimethyl-N-(2-nitrobenzyl)ammonio]-1-[(5',6',7'-trimethoxyindol-2'-yl) carbonyl]indoline chloride (compound 14) as an off-white solid (28%), mp 105–106° C. $^1$H NMR [$(CD_3)_2SO$] δ 11.56 (d, J=2 Hz, 1 H, indole NH), 8.52 (s, 1 H, H-7), 7.98–7.93 (m, 1 H, ArH), 7.79–7.74 (m, 2 H, ArH), 7.62 (d, J=8.6 Hz, 1 H, H-4), 7.52–7.47 (m, 2 H, ArH), 7.11 (d, J=2.1 Hz, 1 H, H-3'), 6.96 (s, 1 H, H-4'), 5.44 (s, 2 H, $NCH_2Ar$), 4.76 (dd, J=10.4, 9.4 Hz, 1 H, H-2), 4.41 (dd, J=10.8, 4.6 Hz, 1 H, H-2), 4.09–3.96 (m, 3 H, $CHCH_2Cl$), 3.91 (s, 3 H, $OCH_3$), 3.82 (s, 3 H, $OCH_3$), 3.79 (s, 3 H, $OCH_3$), 3.67 (s, 6 H, $NMe_2$). Anal. Calculated for $C_{30}H_{32}Cl_2N_4O_6.3H_2O$: 53.6; H, 5.7; N, 8.4. Found: C, 54.1; H, 5.5; N, 8.3%.

EXAMPLE 4c

Preparation of 3-(chloromethyl)-6-[N,N-dimethyl-N-(4-nitrobenzyl)-ammonio]-1-(methanesulfonyl) indoline chloride (compound 11) of General Formula I by the Method Outlined in Scheme 1.

A mixture of 6-amino-3-(chloromethyl)-1-(methanesulfonyl)indoline (29) [Tercel, M., Denny, W. A. and Wilson, W. R., *Bioorg. Med. Chem. Lett.*, 1996, in press] (73 mg, 0.28 mmol), 4-nitrobenzaldehyde (51 mg, 0.34 mmol) and toluenesulfonic acid monohydrate (5 mg, 0.3 mmol) in benzene (30 mL) was heated to reflux and most of the benzene slowly distilled off over 40 min. The remaining orange-brown solution was cyanoborohydride (35 mg, 0.56 mmol) then 2N HCl (0.5 mL) were added and the mixture was stirred at 20 C for 40 min, then evaporated. The residue was diluted with water, extracted with EtOAc (×2), and the extracts dried ($Na_2SO_4$) and evaporated. Dry column chromatography, eluting with EtOAc/petroleum ether (1:2), gave 3-(chloromethyl)-1-(methanesulfonyl)-6-[(4-nitrobenzyl)amino]indoline (30) as a yellow oil (96 mg, 87%). $^1$H NMR (CDCl$_3$) ä 8.19 (d, J=8.8 Hz, 2 H, ArH o to $NO_2$), 7.52 (d, J=8.8 Hz, 2 H, ArH m to $NO_2$), 7.00 (d, J=8.2 Hz, 1 H, H-4), 6.73 (d, J=2.2 Hz, 1 H, H-7), 6.22 (dd, J=8.2, 2.2 Hz, 1 H, H-5), 4.47 (s, 2 H, $NCH_2Ar$), 4.03 (dd, J=10.8, 8.8 Hz, 1 H, CHHN), 3.92 (dd, J=10.8, 4.6 Hz, 1 H, CHHN), 3.69 (dd, J=10.4, 4.1 Hz, 1 H, CHHCl), 3.67–3.60 (m, 1 H, H-3), 3.53 (dd, J=10.4, 7.9 Hz, 1 H, CHHCl), 2.83 (s, 3 H, $NSO_2CH_3$). $^{13}$C NMR ä 148.7, 147.2, 146.8, 143.4, 119.9 (C-6,8,9,1,4), 127.8, 123.9 (C-2 and 6, 3 and 5), 125.7, 107.9, 98.6 (C-4,5,7), 54.6 (C-2), 47.5, 46.8 ($CH_2Cl$, $NCH_2Ar$), 41.9 (C-3), 34.5 ($SO_2CH_3$). MS (DEI, $^{35}$Cl) m/z 395 (35%, M$^+$), 346 (100%, M-$CH_2Cl$); HRMS calcd. for $C_{17}H_{18}ClN_3O_4S$ 395.07066, found 395.06880.

Sodium cyanoborohydnide (40 mg, 0.64 mmol) then 2N HCl (0.5 mL) were added to a solution of 30 (96 mg, 0.24 mmol) and formaldehyde (0.18 mL of a 40% w/v aq. solution, 2.4 mmol) in MeOH (15 mL) and THF (5 mL) and the mixture stirred at 20° C. for 45 min. The solvent was evaporated, the residue was diluted with water and extracted with $CH_2Cl_2$ (×2), and the extracts dried ($Na_2SO_4$) and evaporated. Dry column chromatography (eluting with 1:2 EtOAc:petroleum ether) gave 3-(chloromethyl)-1-(methanesulfonyl)-6-[N-methyl-N-(4-nitrobenzyl)amino] indoline (31) (73 mg, 73%), mp (benzene-petroleum ether) 138–139 C. $^1$H NMR ($CDCl_3$) ä 8.18 (d, J=8.8 Hz, 2 H, ArH o to $NO_2$), 7.39 (d, J=8.8 Hz, 2 H, ArH m to $NO_2$), 7.05 (d, J=8.4 Hz, 1 H, H-4), 6.82 (d, J=2.4 Hz, 1 H, H-7), 6.3 5 (dd, J=8.4 2.4 Hz, 1 H, H-5), 4.63 (s, 2 H, $NCH_2Ar$), 4.04 (dd, J=10.8, 8.8 Hz, 1 H, CHHN), 3.93 (dd, J=10.8, 4.7 Hz, 1 H, CHHN), 3.71 (dd, J=10.4, 4.1 Hz, 1 H, CHHCl), 3.68–3.61 (m, 1 H, H-3), 3.55 (dd, J=10.4, 7.8 Hz, 1 H, CHHCl), 3.11 (s, 3 H, $NCH_3$), 2.81 (s, 3 H, $NSO_2CH_3$). $^{13}$C NMR ä 150.3, 147.1, 146.5, 143.5, 118.9 (C-6,8,9,1,4), 127.4, 123.9 (C-2 and 6, 3 and 5), 125.5, 107.7, 97.9 (C-4,5,7), 56.5, 54.7 (C-2, $NCH_2Ar$), 46.9 ($CH_2Cl$), 41.8 (C-3), 39.5 ($NCH_3$), 34.5 ($SO_2CH_3$). Anal. Calculated for $C_{18}H_{20}ClN_3O_4S$: C, 52.8; H, 4.9; N, 10.3; Cl, 8.7. Found: C, 52.6; H 5.1; N, 10.1; Cl, 8.9%.

A mixture of 31 (79 mg, 0.19 mmol) and trimethyloxonium tetrafluoroborate (105 mg, 0.71 mmol) in $CH_2Cl_2$ (5 mL) was stoppered and stirred at 20 C for 4 days. Water was added and the mixture stirred until most of the oily solid dissolved. The separated organic layer was dried ($Na_2SO_4$) and evaporated, dry column chromatography, eluting with EtOAc/petroleum ether (1:2), gave recovered starting material (24 mg, 30%). The aqueous phase was combined with the remaining oily solid, evaporated, and the residue extracted with MeOH. The resulting crude ammonium salt was converted to the chloride form by ion exchange chromatography on Dowex 50 WX8 resin (1.5 mL), loading the sample in MeOH:water (1:1) and washing until the eluate was neutral, then eluting with 1:1 MeOH:2N HCl (10 mL) followed by MeOH\4N HCl (1:1) (10 mL). The combined eluate was evaporated to give 3-(chloromethyl)-6-[N,N-dimethyl-N-(4-nitrobenzyl)-ammonio]-1-(methanesulfonyl) indoline chloride (11) as a white foam (87 mg). $^1$H NMR ($CD_3OD$) ä 8.17 (d, J=8.2 Hz, 2 H, ArH), 7.63 (br d, J=8.3 Hz, 1 H, H-4 or 5), 7.57 (br d, J=8.3 Hz, 1 H, H-4 or 5), 7.51 (s, 1 H, H-7), 7.41 (d, J=8.2 Hz, 2 H, ArH), 5.22 (s, 2 H, $NCH_2Ar$), 4.32–4.25 (m, 1 H), 4.06–4.01 (m, 2 H), 3.96–3.93 (m, 2 H), 3.75 (s, 6 H, $NMe_2$), 3.02 (s, 3 H, $NSO_2CH_3$). $^{13}$C NMR ä 150.7, 146.0, 145.8, 136.1, 135.7 (C-6,8,9,1,4), 135.3, 124.8 (C-2 and 6, 3 and 5), 128.2, 117.9, 107.6 (C-4,5,7), 73.1 ($NCH_2Ar$), 55.3 (C-2), 54.6 ($NMe_2$), 47.8 ($CH_2Cl$), 42.8 (C-3), 36.4 ($SO_2CH_3$).

EXAMPLE 5a

Preparation of 2-[N-(acridin-4-yl)carbonyl] aminoethyl-(dimethyl)-4-nitrobenzylammonium bromide (compound 15) of General Formula I by the Method Outlined in Scheme 2

A mixture of the free base of N-[(dimethylamino)ethyl] acridine-4-carboxamide (DACA) (37) [Atwell, Rewcastle, Baguley and Denny, *J. Med. Chem.* 30: 664–669, 1987] (1.13 g, 3.86 mmol) and 4-nitrobenzyl bromide (1.84 g, 8.50 mmol) in dry benzene (100 mL) was heated under reflux for 19 h and cooled. The resulting precipitate was filtered off and washed several times with dichloromethane to give 2-[N-(acridin-4-yl)carbonyl]aminoethyl-(dimethyl)-4-nitrobenzyl ammonium bromide (compound 15) (2.0 g, 100%), mp 170–172° C. (dec.). $^1$H NMR [($CD_3$)$_2$SO] d 11.63 (t, J=5.8 Hz, 1H, exchangeable with $D_2O$, NH), 9.38 (s, 1 H, H-9), 8.77 (dd, J=7.1, 1.5 Hz, 1 H, H-3), 8.45 (dd, J=8.4, 1.5 Hz, 1 H, H-1), 8.42 (dd, J=8.8, 1.0 Hz, 1 H, H-5), 8.38 (br d, J=8.7 Hz, 2 H, phenyl H), 8.28 (dd, J=8.3, 1.0 Hz, 1 H, H-8), 7.90 (ddd, J=8.8, 6.6, 1.0 Hz, 1 H, H-6), 7.95 (br d, J=8.7 Hz, 2 H, phenyl H), 7.80 (dd, J=8.4, 7.1 Hz, 1 H, H-2), 7.74 (ddd, J=8.3, 6.6, 1.0 Hz, 1 H, H-7), 4.89 (s, 2 H, $CH_2$), 4.17 (q, collapsed to t after $D_2O$, J=6.4 Hz, 2 H, $NHCH_2$), 3.74 (t, J=6.4 Hz, 2 H, $NHCH_2CH_2$), 3.21 (s, 6 H, $CH_3$). Anal. Calculated for *CRL7459.

EXAMPLE 5b

Preparation of 2-[N-(acridin-4-yl)carbonyl] aminoethyl-(dimethyl)-(5-nitro-2-thienyl) methylammonium chloride (compound 16) of General Formula I by the Method Outlined in Scheme 2

A mixture of the free base of DACA (37) (0.21 g, 0.70 mmol) and 2-chloromethyl-5-nitrothiophene [Newcombe P. J. and Norris R. K. *Aust. J. Chem.* 1979, 32, 2647–58 ](0.12 g, 0.67 mmol) in benzene (20 mL) was stirred at reflux temperature for 53 h. Cooling the mixture to room temperature gave a precipitate of 2-[N-(acridin-4-yl)carbonyl] aminoethjyl-(dimethyl)-(5-nitro-2-thienyl) methylammonium chloride (compound 16) (0.27 g, 86%), which was collected and washed with $CH_2Cl_2$, mp 180–182° C. (dec.) $^1$H NMR [($CD_3$)$_2$SO] δ 11.64 (t, J=6.0 Hz, 1 H, exchangeable with $D_2O$, NH), 9.38 (s, 1 H, H-9), 8.76 (dd, J=7.0, 1.4 Hz, 1 H, H-3), 8.46 (d, J=8.0 Hz, 1 H, H-5), 8.44(dd, J=8.0, 1.4 Hz, 1 H, H-1), 8.27 (br s, J=8.0 Hz, 1 H, H-8), 8.22 (d, J=4.2 Hz, thienyl H-4), 8.00 (td, J=8.0, 1.0 Hz, 1 H, H-6), 7.80 (dd, J=8.0, 7.0 Hz, 1 H, H-2), 7.74(t, J=8.0 Hz, 1 H, H-7), 7.63 (d, J=4.2 Hz thienyl H-3), 5.12 (s, 2 H, thienyl-$CH_2$), 4.16 (q, J=6.0 Hz, 2 H, collapsed to a t after $D_2O$, $NHCH_2$), 3.77 (t, J=6.0 Hz, 2 H, $NHCH_2CH_2$), 3.27 (s, 6 H, $CH_3$). Anal. Calculated for $C_{23}H_{23}ClN_4O_3S$: C, 58.7; H, 4.9; N, 11.9; Cl, 7.5. Found: C, 58.2; H, 5.3; N, 11.5; Cl, 7.6%.

EXAMPLE 5c

Preparation of 2-[N-(9-amino-5-methylacridin-4-yl) carbonyl]aminoethyl-(dimethyl)-4-nitrobenzylammonium bromide (compound 17) of General Formula I by the Method Outlined in Scheme 2

Reaction of the free base of (N,N-dimethylaminoethyl)-9-amino-5-methylacridine-4-carboxamide (AMAC) (38) (for preparation see Rewcastle, Atwell, Chambers, Baguley and Denny, *J. Med. Chem.*, 29, 472–477, 1986) with 4-nitrobenzyl bromide in dry benzene [using the procedure of Example 5a] gave 2-[N-(9-amino-5-methylacridin-4-yl) carbonyl]aminoethyl-(dimethyl)-4-nitrobenzylammonium bromide (compound 17) in 95% yield, mp 197–199° C. (dec.). $^1$H NMR [($CD_3$)$_2$SO)] δ 12.95(t, J=6.0 Hz, 1 H, exchangeable with $D_2O$, CONH), 4.10 (br q, collapsing to a t after $D_2O$, J=7.0 Hz, 2 H, $CONHCH_2$), 3.66 (t, J=7.0 Hz, 2 H, $CONHCH_2CH_2$), 8.66 (d, J=7.5 Hz, 2 H, H-1,3), 8.37 (br d, J=8.8 Hz, 2 H, ArH), 8.33 (d, J=8.6 Hz, 1 H, H-8), 8.23 (br s, 2 H, exchangeable with $D_2O$, $NH_2$), 7.93 (br s, J=8.8 Hz, 2 H, ArH), 7.69 (d, J=6.7 Hz, 1 H, H-6), 7.47 (t, J=7.5 Hz, 1 H, H-2), 7.32 (dd, J=8.6, 6.7 Hz, 1 H, H-7), 4.83 (s, 2 H, $ArCH_2$), 3.15 (s, 6 H, $NCH_3$), 2.74 (s, 3 H, $ArCH_3$). Anal. Calcd. for $C_{26}H_{28}BrN_5O_3 \cdot H_2O$: C, 56.1; H, 5.4; N, 12.6. Found: C, 56.6; H, 5.4, N, 12,4%.

EXAMPLE 5d

Preparation of 2-[N-(9-amino-5-methylacridin-4-yl) carbonyl]aminoethyl-(dimethyl)-2-nitrobenzyl] ammonium chloride (compound 18) of General Formula I by the Method Outlined in Scheme 2

A mixture of AMAC (38) (0.15 g, 0.47 mmol) and 2-nitrobenzyl chloride (0.19 g, 1.12 mmol) in MeCN (10 mL) was stirred under reflux for 3 d. The mixture was then cooled to room temperature and the orange solid filtered off, washed with $CH_2Cl_2$ and dried to give pure (98% by HPLC) 2-[N-(9-amino-5-methylacridin-4-y)carbonyl]aminoethyl-(dimethyl)-2-nitrobenzyl-ammonium chloride (compound 18) (0.22 g, 94%), mp 264–266° C. Repeated recrystallization from $MeOH/Et_2O$ or MeOH/EtOAc gave material of 99+% purity. $^1H$ NMR [$(CD_3)_2SO$] δ 12.94 (t, J=6.0 Hz, 1 H, exchangeable with $D_2O$, CONH), 8.69–7.31 (m, 10 H, ArH), 8.25 (s, 2 H, exchangeable with $D_2O$, $NH_2$), 5.05 (s, 2 H, benzylic $CH_2$), 4.07 (br q, J=6.0 Hz, 2 H, collapsed to a t after $D_2O$, J=6.9 Hz, CONH $CH_2$), 3.74 (t, J=6.9 Hz, 2 H, CONH$CH_2CH_2$), 3.12 (s, 6 H, $NCH_3$), 2.74 (s, 3 H, $CH_3$). Anal. Calculated for $C_{26}H_{28}ClN_5O_3$: C, 63.2; H, 5.7; N, 14.2; Cl, 7.2. Found: C, 63.3; H, 5.5; N, 14.4; Cl, 7.5%.

EXAMPLE 5e

Preparation of 2-[N-(9-amino-5-methylacridin-4-yl) carbonyl]aminoethyl-(dimethyl)-5-nitro-2-thienylmethylammonium chloride (compound 19) of General Formula I by the Method Outlined in Scheme 2

Reaction of AMAC (38) (0.16 g, 0.50 mmol) and 2-chloromethyl-5-nitrothiophene [for preparation see Newcombe, P. J. and Norris, R. K. *Aust. J Chem.* 1979, 32, 2647–2658] (0.18 g, 1.00 mmol) under reflux for 16 h [as described for the preparation of SN 26208 above] gave 2-[N-(9-amino-5-methylacridin-4-yl)carbonyl]aminoethyl-(dimethyl)-5-nitro-2-thienylmethyl-ammonium chloride (compound 19) as a hydrochloride salt (0.21 g, 78%), mp 205° C. (dec). $^1H$ NMR [$(CD_3)_2SO$] δ 14.32 (s, 1 H, exchangeable with $D_2O$), HCl), 10.38–10.34 (2s, 2 H, exchangeable with $D_2O$, $NH_2$), 10.10 (br.t, J=5.5 Hz, 1 H, exchangeable with $D_2O$, CONH), 9.02 (d, J=8.0 Hz, 1 H, H-3), 8.83 (d, J=8.0 Hz, 1 H, H-1), 8.61 (d, J=8.5 Hz, 1 H, H-8), 8.21 (d, J=4.2 Hz, 1 H, thienyl H-4), 7.98 (d, J=7.1 Hz, 1 H, H-6), 7.76 (t, J=8.0 Hz, 1 H, H-2), 7.62 (d, J=4.2 Hz, 1 H, thienyl H-3), 7.58 (dd, J=8.5, 7.1 Hz, 1 H, H-7), 5.08 (s, 2 H, thienyl $CH_2$), 3.98 (br q, J=5.5 Hz, collapsing to a t after $D_2O$, 2 H, J=6.4 Hz, CONH$CH_2$), 3.73 (t, J=6.4 Hz, 2 H, CONH$CH_2CH_2$), 3.23 (s, 6 H, $NCH_3$), 2.69 (s, 3 H, Ar$CH_3$). Anal. Calculated for $C_{24}H_{26}ClN_5O_3S.HCl$: C, 53.7; H, 5.1; N, 13.1. Found: C, 53.5; H,, 5.8; N, 12.8%.

EXAMPLE 5f

Preparation of 2-[N-(9-amino-5-methylacridin-4-yl) carbonyl]aminoethyl-(dimethyl)-2-[4-morpholino-5-nitro-4-thiazolylmethyl]ammonium chloride (compound 20) of General Formula I by the Method Outlined in Scheme 2

A solution of 2-(4-morpholino)-5-nitrothiazole (39) [for preparation see Lee, H. H.; Palmer, B. D.; Boyd, M. and Denny, W. A. *J. Heterocycl. Chem.* in press] (6.57 g, 30.6 mmol) and tert-butyl 2,2-dichloroacetate (8.50 g, 45.9 mmol) in DMF (50 mL) was added slowly to a stirred mixture of potassium tert-butoxide (12.0 g, 107 mmol) and dry DMF (50 mL) at −40° C. under $N_2$. The mixture was stirred for a further 1.5 h while the temperature allowed to rise to slowly to −10° C. It was then poured into excess 1% aqueous HCl, and extracted with EtOAc. Workup of the organic layer gave an orange solid which was triturated with $MeOH/H_2O$ (1:3), then filtered off and dried to give tert.-butyl 2-chloro-2-[2-(4-morpholino)-5-nitro-4-thiazolyl] acetate (40) (10.7 g, 95%), mp (EtOAc) 163–165° C. $^1H$ NMR ($CDCl_3$) δ 6.15 (s, 1 H, CH), 3.9–3.5 (m, (8 H, morpholino H), 1.48 (s, 9 H, $CH_3$). Anal. Calculated for $C_{13}H_{18}ClN_3O_5S$: C, 42.9; H, 5.0; N, 11.6; Cl, 9.7. Found: C, 42.6; H, 5.2; N, 11.6; Cl, 10.0%.

A solution of the above acetate (40) (10.7 g, 29.3 mmol) in AcOH (300 mL) was heated under reflux for 1.5 h, then cooled, concentrated under reduced pressure to ca. 50 mL, and poured into ice-water. Extraction with EtOAc and chromatography of the crude product on silica gel, eluting with EtOAc/petroleum ether (1:4), gave 4-chloromethyl-2-(4-morpholino)-5-nitrothiazole (41) (2.99 g, 39%), mp (EtOAc/petroleum ether) 119–121° C. $^1H$ NMR ($CDCl_3$) δ 4.87 (s, 2 H, $CH_2Cl$). 4.0–3.5 (m, 8 H, morpholino H). Anal. Calculated for $C_8H_{10}ClN_3O_3S$: C, 36.4; H, 3.8; N, 15.9; Cl, 13.4. Found: C, 36.7; H, 3.7; N, 15.8; Cl, 13.6%.

A mixture of the above chloride (41) (0.40 g, 1.50 mmol) and AMAC (31) (0.16 g, 0.50 mmol) was heated under reflux for 3 days using the procedure described above gave a crude product which was chromatographed on a short column of silica gel. Elution with $CHCl_3/MeOH/Et_3N$ (5:1:2) gave 2-[N-(9-amino-5-methylacridin-4-yl)carbonyl] aminoethyl-(dimethyl)-(2-[4-morpholino-5-nitro-4-thiazolyhnethyl]ammonium hydroxide (compound 20) (0.27 g, 95%), mp ($MeOH/Et_2O$) 133° C. (dec.). $^1H$ NMR [$(CD_3)_2SO$] δ 12.97 (t, J=5.8 Hz, 1 H, exchangeable with $D_2O$, CONH), 7.3–8.6 (m 6 H, ArH), 8.19 (s, 2 H, exchangeable with $D_2O$, $NH_2$), 6.58 (s, 1 H, exchangeable with $D_2O$, OH), 5.01 (s, 2 H, thiazolyl $CH_2$), 3.50–4.20 (m, 12 H, $CH_2CH_2$ and morpholino H), 3.45 (s, 6 H, $NCH_3$), 2.63 (s, 3 H, Ar$CH_3$). Anal. Calculated for $C_{27}H_{33}N_7O_5S.0.5H_2O$: C, 56.2; H, 5.9; N, 17.0. Found: C, 56.3; H, 6.6; N, 17.0%. Treatment of a solution of the above hydroxide in MeOH with excess concentrated HCl gave the hydrochloride salt (compound 16), mp 244–246° C. (dec.).

EXAMPLE 5g

Preparation of 2-(N-[9-amino-5-methylacridin-5-yl] carbonyl)aminoethyl-(dimethyl)[1-methyl-5-nitro-2-pyrrolyl]methylammonium chloride (compound 21) of General Formula I by the Method Outlined in Scheme 2

Solid $NaBH_4$ (0.19 g, 5.03 mmol) was added portionwise to a stirred solution of 1-methyl-5-nitro-2-pyrrolealdehyde (42) [for preparation see Fournari, P. *Bull. Soc. Chim. Fr.*, 88, 488–491, 1963] (0.78 g, 5.07 mmol) in MeOH (40 mL) at room temperature under $N_2$. After addition was complete, the reaction mixture was stirred for a further 20 min, then water (40 mL) was added and the mixture was saturated with solid $K_2CO_3$. Extraction with EtOAc gave 2-hydroxymethyl-1-methyl-5-nitropyrrole (43) (0.77 g, 97%), mp (EtOAc/petroleum ether) 76–77° C. $^1H$ NMR ($CDCl_3$) δ 7.16 (d, J=4.3 Hz, 1 H, H-4), 6.17 (d, J=4.3 Hz, 1 H, H-3), 4.68 (s, 2 H, $CH_2$), 4.02 (s, 3 H, $CH_3$). Anal. Calculated for $C_6H_8N_2O_3$: C, 45.1; H, 5.2; N, 17.9. Found: C, 46.1; H, 5.1; N, 17.6%.

A stirred solution of the above alcohol (43) (0.13 g, 0.83 mmol) in dry $CH_2Cl_2$ (5 mL) at 0° C. was treated with methanesulfonyl chloride (0.36 mL. 1.25 mmol), followed by $Et_3N$ (0.50 mL). After stirring at 0° C. for 15 min, the mixture was evaporated to dryness under reduced pressure at room temperature, and the resulting brown solid was partitioned between water and EtOAc. Workup of the organic layer gave a crude product which was was chromatographed on silica gel. Elution with $CH_2Cl_2$/petroleum ether (1:1) gave 1-methyl-2-chloromethyl-5-nitropyrrole (44) (0.13 g, 88%), mp (EtOAc/petroleum ether) 82.5–83.5° C. $^1$H NMR ($CDCl_3$) δ 7.16 (d, J=4.4 Hz, 1 H, H-4), 6.26 (d, J=4.4 Hz, 1 H, H-3), 4.60 (s, 2 H, $CH_2Cl$), 4.02 (s, 3 H, $CH_3$). Anal. Calculated for $C_6H_7ClN_2O_2$: C, 41.3; H, 4.0; N, 16.0. Found: C, 41.4; H, 4.0; N, 15.9%.

Reaction of the above chloride (44) (0.18 g, 1.00 mmol) and AMAC (38) (0.16 g, 0.50 mmol) as described in Example 5a above gave 2-(N-[9-amino-5-methylacridin-5-yl]carbonyl)aminoethyl(dimethyl)[1-methyl-5-nitro-2-pyrrolyl]methylammonium chloride (compound 21) in quantitative yield, mp (MeOH/EtOAc) 188–190° C. (dec.). $^1$H NMR [$(CD_3)_2SO$]δ 12.98 (t, J=6.0 Hz, 1 H, exchangeable with $D_2O$, CONH), 8.69 (d, J=8.5 Hz, 1 H, H-3), 8.65 (d, J=7.2 Hz, 1 H, H-1), 8.35 (d, J=8.6 Hz, 1 H, H-8), 8.28 (s, 2 H, exchangeable with $D_2O$, $NH_2$), 7.69 (d, J=6.8 Hz, 1 H, H-6), 7.46 (dd, J=8.5, 7.2 Hz, 1 H, H-2), 7.36 (d, J=4.5 Hz, 1 H, pyrrolyl H-4), 7.32 (dd, J=8.6, 6.8 Hz, 1 H, H-7), 6.74 (d, J=4.5 Hz, 1 H, pyrrolyl H-3), 4.89 (s, 2 H, pyrrolyl $CH_2$), 4.08 (q, J=6.0 Hz, collapsed to a t after $D_2O$, J=6.8 Hz, 2 H, $CONHCH_2$), 4.01 (s, 3 H, pyrrolyl $CH_3$), 3.72 (t, J=6.8 Hz, 2 H, $CONHCH_2$), 3.16 (s, 6 H, $NCH_3$), 2.75 (s, 3 H, $ArCH_3$). Anal. Calculated for $C_{25}H_{29}ClN_6O_3 \cdot 0.5H_2O$: C, 59.3; H, 6.0; N, 16.6. Found: C, 59.4, H, 6.7; N, 16.6%.

EXAMPLE 5h

Preparation of 2-(N-[9-amino-5-methylacridin-4-yl]carbonyl)aminoethyl-(dimethyl)-(1-methyl-4-nitro-5-imidazolyl)methylammonium chloride (compound 22) of General Formula I by the Method Outlined in Scheme 2

Reaction of 1-methyl-4-nitro-5-imidazolyl)methyl chloride [for preparation see M. Makosza and M. Bialecki, *Synlett.*, 181–182, 1991] (0.35 g, 1.00 mmol) and AMAC (38) (0.16 g, 0.50 mmol) under reflux for 3 days as described as in Example 5a above gave 2-(N-[9-amino-5-methylacridin-4-yl]carbonyl)aminoethyl-(dimethyl)-(1-methyl-4-nitro-5-imidazolyl)methylammonium chloride (compound 22) (0.20 g, 80%), mp (MeOH/EtOAc) 245° C. (dec.). $^1$H NMR [$(CD_3)_2SO$] δ 13.0 (t, J=6.0 Hz, 1 H, exchangeable with $D_2O$, $CONH_2$), 8.66 (m, 2 H, H-1, H-3), 8.33 (d, J=8.6 Hz, 1 H, H-8), 8.24 (s, 2 H, exchangeable with $D_2O$, $NH_2$), 8.12 (s, 1 H, imidazolyl H-2), 7.70 (d, J=6.7 Hz, 1 H, H-6), 7.46 (dd, J=8.3, 7.4 Hz, 1 H, H-2), 7.32 (dd, J=8.6, 6.7 Hz, 1 H, H-7), 4.09 (q, J=6.0 Hz, collapsed to a t, J=6.5 Hz, 2 H, $COHNCH_2$), 3.89 (t, J=6.5 Hz, 2 H, $CONHCH_2CH_2$), 3.87 (s, 3 H, imidazolyl $CH_3$), 3.20 (s, 6 H, $NCH_3$), 2.76 (s, 3 H, $ArCH_3$). Anal. Calculated for $C_{24}H_{28}ClN_7O_3 \cdot H_2O$: C, 55.9; H, 5.9; N, 19.0. Found: C, 56.4; H, 6.3; N, 19.1%.

EXAMPLE 5i

Preparation of 2-(N-[9-amino-5-methylacridin-4-yl]carbonyl)aminoethyl-(dimethyl)-(3-nitro-2-thienyl)methylamonium chloride (compound 23) of General Formula I by the Method Outlined in Scheme 2

A mixture of AMAC (38) (0.16 g, 0.50 mmol) and 2-bromomethyl-3-nitrothiophene (0.17 g, 0.75 mmol) in meCN (10 mL) was heated under reflux for 21 h, giving an orange precipitate. The mixture was cooled to room temperature and the precipitate was collected and washed with EtOAc, then dissolved in MeOH/water (1:) and treated with a large excess of Biorad AG 1-X4 ion exchange resin ($Cl^-$ form) for 2 h. Filtration and evaporation of the filtrate gave 2-(N-[9-amino-5-methylacridin-4-yl]carbonyl)aminoethyl-(dimethyl)-(3-nitro-2-thienyl)methylammonium chloride (compound 23) (0.25 g, 100%), mp (MeOH/EtOAc) 190° C. (dec.) $^1$H NNR [$(CD_3)_2SO$] δ 14.31 (s, 1H, exchangeable with $D_2O$), Hcl), 10.50 (s, 1H, exchangeable with $D_2O$, $NH_2$), 10.44 (s, 1H, exchangeable with $D_2O$, $NH_2$), 10.21 (t, J=5.4 Hz, collapsing to a t after $D_2O$, 1H, CONH), 9.08 (t, J=8.4 Hz, 1H, H-3), 8.86 (d, J=7.1 Hz 1 H, H-1), 8.66 (d, J=8.5 Hz, 1H, H-8) 8.06 (d, J=5.7 Hz, 1H, thienyl H-5), 7.97 (d, J=7.0 Hz, 1H, H-6), 7.86 (d,J=6.7 Hz, 1H, thienyl H-4), 7.74 (dd, J=8.4, 7.1 Hz, 1H, H-2), 7.56 (dd, J=8.5, 7.0 Hz, 1H, H-7), 5.33 (s, 2H, $CH_2$), 3.97 (br q, J=5.4 Hz, collapsing to a t after $D_2O$), 2H, $CONHCH_2$), 3.87 (t, J=5.5 Hz, 2H, $CONHCH_2CH_2$), 3.27 (s, 6H, $N(CH_3)_2$), 2.69 (s, 3 H, $ArCH_3$).

EXAMPLE 6a

Preparation of 1,4-bis[((2-(4-nitrobenzyl)dimethylammonium)-ethyl)amino]-9,10-anthracenedione dichloride (compound 24) of General Formula I by the Method Outlined in Scheme 3

A mixture of 1,4-bis(2-dimethylaminoethylamino)-9,10-anthracenedione (45) [for preparation see Zee-Cheng and Cheng, *J. Med. Chem.* 1978, 21, 291–294] (0.19 g, 0.50 mmol) and 4-nitrobenzyl chloride (86 mg, 0.50 mmol) in acetonitrile (50 mL) was stirred under reflux for 30 h, then cooled and evaporated to dryness under reduced pressure. The resulting deep blue solid was chromatographed on silica gel, and elution with acetonitrile/water/AcOH (10:1:1). The appropriate fractions were pooled and evaporated, and the residue was extracted with EtOAc/MeOH (10:1) and filtered. On standing the filtrate deposited 1,4-bis[((2-(4-nitrobenzyl)dimethylammonium)ethyl)amino]-9,10-anthracenedione dichloride (compound 24) (132 mg, 36%), mp 245° C. (dec.). $^1$H NMR [$(CD_3)_2SO$] δ 10.66 (t, J=6.0 Hz, 2 H, exchangeable with $D_2O$, NH), 8.39 (d, J=8.8 Hz, 2 H, ArH), 8.24 (m, 2 H, H-5,8), 7.91 (d, J=8.8 Hz, 2 H, ArH), 7.85 (m, 2 H, H-6,7), 7.62 (s, 2 H, H-2,3), 4.85 (s, 2 H, $CH_2$), 4.10 (q, J=6.0 Hz, 4 H, collapsed to at after $D_2O$, $NHCH_2$), 3.71 (t, J=6.0 Hz, 4 H, $NHCH_2CH_2$), 3,10 (s, 12 H, $NCH_3$). Anal. Calculated for $C_{36}H_{40}Cl_2N_6O_6 \cdot H_2O$: C, 58.3; H, 5.7; N, 11.3; Cl, 9.6. Found: C, 58.8; H, 5.9; N, 11.2; Cl, 9.8%.

EXAMPLE 6b

Preparation of 1-(2-(4-nitrobenzyl)dimethylaminoethylammonium)-4-(2-dimethylamino)ethylammino-9,10-anthracenedione acetate (compound 25) of General Formulla I by the Method Outlined in Scheme 3

Later fractions eluted from the column in Example 6a were also pooled and evaporated, and the residue was extracted with EtOAc/$CH_2Cl_2$ (2:1) and filtered. On cooling the filtrate deposited 1-(2-(4-nitrobenzyl)dimethylaminoethylammonium)-4-(2-dimethylaminoethyl-amino)-9,10-anthracenedione acetate (compound 25) (117 mg, 38%), mp 124–125° C. $^1$H NMR [$(CD_3)_2SO$] δ 10.65 (m, 3 H, exchangeable with $D_2O$, NH and COOH), 8.39 (d, J=8.7 Hz, 2 H, ArH), 8.25 (m, 2 H, H-5,8), 7.92 (d, J=8.7 Hz, 2 H, ArH), 7.85 (m, 2 H, H-6,7), 7.69 (d, J=9.8 Hz, 1 H,H-3), 7.62 (d, J=9.8 Hz, 1 H, H-2), 4.12 (q, J=6.5 Hz, 2 H, collapsed to a t after $D_2O$, $NHCH_2$), 3.94 (q, J=6.5 Hz, 2 H, collapsed to a t after $D_2O$, $NHCH_2$), 3.71 (t, J=6.5 Hz, 2 H, $CH_2N$), 3.15 (s, 6 H, $NCH_3$), 2.84 (s, 6 H, $NCH_3$), 2.49 (s, 3 H, $CH_3CO$). Anal. Calculated for $C_{31}H_{37}N_5O_6.0.5H_2O$: C, 63.7; H, 6.6; N, 12.0. Found: C, 63.9; H, 7.1; N, 12.0%.

EXAMPLE 6c

Preparation of 1,4-bis[[2-(4-nitrobenzyl)dimethyl-ammonium)ethylamino]-5,8-dihydroxy-9,10-anthracenedione dichloride (compound 26) of General Formula I by the Method Outlined in Scheme 3

Leuco-1,4,5,8-tetrahydroxyanthraquinone was prepared from conumercially-available 1,5-diamino-4,8-dihydroxyanthraquinone by the published method [Chang, P. and Cheng, C. C. Synth. Comm., 25, 1893–1900, 1995], and this was converted to 1,4-bis[(2-dimethylamino)-ethylamino]-5,8-dihydroxy-9,10-anthracenedione (46) by the published method [see Murdock, K. C., Wallace, R. E., Durr, F. E., Childs, R. G., Citarella, R. V., Fabio, F. B. and Angier, R. B. J. Med. Chem., 22, 1024–1030, 1979]. A mixture of (46) (0.824 g, 2.00 mmol) and 4-nitrobenzyl chloride (3.44 g, 10.0 mmol) in MeCN (280 mL) were stirred at reflux temperature for 7 d. The solution was then evaporated to dryness under reduced pressure and the residue was purified by chromatography on silica gel, eluting with MeCN/water/AcOH (10:1:1). The appropriate fractions were pooled and evaporated to give a residue which was extracted with EtOAc/MeOH (10:1) and filtered. On cooling the filtrate deposited 1,4-bis[[2-(4-nitrobenzyl)dimethyl-ammonium)ethylamino]-5,8-dihydroxy-9,10-anthracenedione dichloride (compound 26), (0.34 g, 23%), mp (EtOAc/MeOH) 227–229° C. $^1$H NMR [$(CD_3)_2SO$] δ 13.44 (s, 2 H, exchangeable with $D_2O$, OH), 10.45 (br s, 2 H, exchangeable with $D_2O$, NH), 8.39 (d, J=8.6 Hz, 4 H, ArH), 7.92 (d, J=8.6 Hz, 4 H, ArH), 7.70 (s, 2 H, H-6,7), 7.25 (s, 2 H, H-2,3), 4.86 (s, 4 H, $CH_2Ar$), 4.15 (br q, 4 H, collapsed to a t after $D_2O$, J=6.0 Hz, $NHCH_2$), 3.73 (t, J=6.0 Hz, 4 H, $CH_2N$), 3.15 (s, 12 H, $CH_3$. Anal. Calculated for $C_{36}H_{48}Cl_2N_6O_8.H_2O$: C, 55.9; H, 5.5; N, 10.9; Cl, 9.2. Found: C, 55.9; H, 5.4; N, 10.5; Cl, 9.2%.

EXAMPLE 6d

Preparation of 1-[(2-(4-nitrobenzyl)dimethylammonium)ethylamino]-4-[(2-dimethylamino)ethylamino]-5,8-dihydroxy-9,10-anthracenedione chloride (compound 27) of General Formula I by the Method Outlined in Scheme 3

Continued elution of the column in Example 6c gave 1-[(2-(4-nittobenzyl)dimethylammonium)-ethylamino]-4-[(2-dimethylamino)ethylamino]-5,8-dihydroxy-9,10-anthracenedione chloride (compound 27) (0.73 g, 62%), mp (EtOAc/MeOH) 136–138° C. $^1$H NMR ($CD_3OD$) δ 8.40 (br s, 2 H, ArH), 7.89 (br s, 2 H, ArH), 7.43 (s, 2 H, H-6,7), 7.12 (s, 2 H, H-2,3), 4.13 (br s, 2 H, $NHCH_2$), 3.77 (br s, 2 H, $NHCH_2$), 3.62 (br s, 2 H, $CH_2N$), 3.25 (s, 6 H, $CH_3$), 2.78 (br s, 2 H, $CH_2N$), 2.43 (s, 6 H, $CH_3$). Anal. Calculated for $C29H_{35}Cl_2N_5O_6$: C, 56.1; H, 5.7; N, 11.3; Cl, 11.4. Found: C, 55.6; H, 6.1; N, 11.0; Cl, 11.2%.

EXAMPLE 7a

Preparation of bis(3-methyl-2,4-pentanedionato)(N-[3-[(2-aminoethyl)-amino]propyl]acridine-4-carboxamide)cobalt(III) perchlorate, (compound 28) of General Formula I by the Method Outlined in Scheme 4

N-[3-[(2-Aminoethyl)amino]propyl]acridine-4-carboxamide trihydrochloride (47) [for preparation see Lee H H, Palmer B D, Baguley B C, Chin M, McFadyen W D, Wickham, G, Thorsbourne-Palmer D, Wakelin L P G and Denny V A. J. Med. Chem. 35, 2983–2987, 1992] (0.200 g, 0.445 mmol) was suspended in a solution containing $Co(Mecac)_3$ (0.177 g, 0.445 mmol) dissolved in MeOH (5 ml). A 1.0 M solution of KOH in MeOH (1.33 ml, 3 eq.) was added followed immediately by charcoal (0.100 g). The mixture was stirred at ambient temperature for 2 h, then filtered through Celite and the collected charcoal washed with a portion of MeOH. The combined filtrate plus washings were combined with aqueous 3 M $NaClO_4$ and extracted with $CH_2Cl_2$ (3×). The purple-red organic phase was evaporated to dryness and chromatographed on silica gel. Elution with acetone/$CH_2Cl_2$ (progressively increasing concentration of acetone up to 50%) eluted two nearly resolved reddish purple bands. In each case the solvent was removed under reduced pressure to give a purple residue (1st band=36 mg, 2nd band=140 mg). These compounds are the two diastereoisomers (enantiomeric pairs: Δ(S), Λ(R) and Δ(R), Λ(S)) of bis(3-methyl-2,4-pentanedionato)(N-[3-[(2-aminoethyl)amino]propyl]acridine-4-carboxamide)cobalt (III) perchlorate (28) (176 mg, 56.1%) $^1$H NMR ($CDCl_3$) δ 11.91 (br t, 1H, NHCO, J=6.0 Hz), 8.93 (s, 1H, H-9), 8.71 (d-d, 1H, H-5, J=7.0, 1.2 Hz), 8.22 (d, 1H, H-1), 8.19 (d, 1H, H-8), 8.06 (d, 1H, H-3, J=8.4 Hz), 7.89 (t-d, 1H, H-6, J=7.0, 1.1 Hz), 7.66 (t, 1H, H-7, J=7.7 Hz), 7.63 (t, 1H, H-2, J=7.6 Hz), 4.95 (br, 1H, NH), 4.07 (br q, 1H, NH, J=7.3 Hz), 3.91, 3.60 (m, 1H, $CH_2NHCO$), 3.39 (br d, 1H, NH, J=8.2 Hz), 3.03 (m, 2H, $CH_2NHR$), 2.97, 2.80 (m, 1H, $CH_2NHR$), 2.87 (m, 2H, $CH_2NH_2$), 2.31, 2.19, 2.10, 1.82 (s, 3H, $CH_3CO$), 2.25, 2.07 (m, 1H, $CH_2CH_2CH_2$), 1.67, 1.63 (s, 3H, $CH_3$—C). $^{13}$C NMR ($CDCl_3$) δ 188.79, 2× 188.01, 187.66 (CO), 166.92 (CONH), 147.61, 145.96 (C-12,13), 138.16 (C-9), 135.08, 132.96 (C-1,8), 131.90 (C-5), 128.91, 128.17 (C-3, 6), 127.32, 126.04 (C-11,14), 126.70, 125.08 (C-2,7); 101.82, 101.78 (C—$CH_3$), 51.67, ($CH_2NHCO$), 43.95, 43.09 ($CH_2NHR$), 35.80 ($CH_2NH_2$), 26.72, 26.55, 26.22, 25.83 ($CH_3CO$), 26.51 ($CH_2CH_2CH_2$), 15.15, 15.00 ($CH_3$-C). HRMS (FAB$^+$) Calc. for $C_{31}H_{40}N_4O_5Co$; 607.2331. Found 317.607.2354.

EXAMPLE 8

Preparation of Cyclopropylindole Precursors 32

A solution of 4-chloro-3-nitrobenzoic acid (10.03 g, 50 mmol), $SOCl_2$ (4.4 mL, 60 mmol) and DMF (4 drops) in 1,2-dichloroethane (150 mL) was stirred under reflux for 14 h, cooled and evaporated. The resulting crude acid chloride was dissolved in THF (100 mL), cooled to 0° C., and a solution of potassium t-butoxide (5.57 g, 50 mmol) in THF (150 mL) was added dropwise over 30 min under nitrogen. The mixture was stirred a further 15 min at 0° C., diluted with aqueous $NaHCO_3$ and extracted with EtOAc (×2), and the extracts were dried ($Na_2SO_4$) and evaporated. Flash chromatography of the residue on silica gel (petroleum ether/EtOAc; 30:1) gave t-butyl 4-chloro-3-nitrobenzoate as a white crystalline solid (11.45 g, 89%), mp (petroleum ether) 70–71° C. $^1$H NMR ($CDCl_3$) d 8.42 (d, J=2.0 Hz, 1 H, H-2), 8.11 (dd, J=8.4, 2.0 Hz, 1 H, H-6), 7.61 (d, J=8.4 Hz, 1 H, H-5), 1.61 (s, 9 H, t-Bu). Anal. Calculated for $C_{11}H_{12}ClNO_4$: 51.3; H, 4.7; N, 5.4; Cl, 13.8. Found: C, 51.6; H, 4.8; N, 5.4; Cl, 14.0%.

Sodium hydride (13.5 g of a 60% dispersion in oil, 0.34 mol) was washed with petroleum ether (×3) under nitrogen and suspended in dry THF (400 mL). A solution of dimethyl malonate (40.4 mL, 0.35 mol) in THF (50 mL) was added dropwise over 45 min with water-bath cooling, keeping the internal temperature below 30° C., and the resulting gel was broken up with more dry THF (300 mL). The above t-Butyl 4-chloro-3-nitrobenzoate (21.7 g, 84 mmol) was added and the mixture was stirred at reflux under nitrogen for 15 h. The red-brown solution was cooled, poured into water, and aqueous HCl (2 N, ca. 60 mL) added slowly until the red nitronate color was dispersed. The THF was evaporated and the aqueous phase extracted with $CH_2Cl_2$ (×3), the extracts were dried ($Na_2SO_4$) and evaporated. Formic acid (100 mL) was added to the residue and the mixture was stirred at 50° C. for 4 h (when tlc analysis showed no remaining t-butyl ester). The formic acid was evaporated and the residue was taken up in EtOAc and washed with water (×3). The organic layer was extracted with aqueous $NaHCO_3$ (×2), and the aqueous phase was acidified (conc. HCl), and extracted with $CH_2Cl_2$ (×2). The organic layer was dried ($Na_2SO_4$), evaporated, and the resulting cream solid recrystallized from benzene (ca. 250 mL) to give dimethyl (4-carboxy-2-nitrophenyl)malonate as cream prisms (21.8 g, 87%), mp 147–149° C. $^1$H NMR (($CD_3$)$_2$SO) d 13.77 (br s, 1 H, $CO_2$H), 8.52 (d, J=1.7Hz, 1 H, H-3), 8.28 (dd, J=8.1, 1.7 Hz, 1 H, H-5), 7.70 (d, J=8.1 Hz, 1 H, H-6), 5.62 (s, 1 H, ArCH), 3.71 (s, 6 H, $CO_2$Me); $^{13}$C NMR (($CD_3$)$_2$SO) d 166.9, 165.1, 148.2, 134.0, 133.1, 132.3, 132.1, 125.5 ($CO_2$Me, C-1,2,3, 4,5,6), 54.3 (ArCH), 52.9 (OMe). Anal. Calculated for $C_{12}H_{11}NO_8$: C, 48.5; H, 3.7; N, 4.7. Found: C, 48.7; H, 3.5; N, 4.7%.

A solution of the above malonate (3.44 g, 11.6 mmol), $SOCl_2$ (1.0 mL, 13.9 mmol) and DMF (4 drops) in 1,2-dichloroethane (60 mL) was stirred under reflux for 1 h, cooled and evaporated. The residue was dissolved in $Me_2CO$ (30 mL) and added dropwise over 10 min to a vigorously stirred solution of sodium azide (2.26 g, 35 mmol) in water (30 mL) and M acetone (100 mL) at 0° C. After a further 30 min at 0° C., EtOAc (100 mL) was added, most of the $Me_2CO$ was evaporated, and the EtOAc layer was washed with water, dried ($Na_2SO_4$), and evaporated. The residue was dissolved in dry toluene (35 mL) and stirred at reflux for 40 min. Benzyl alcohol (2.2 mL, 21 mmol) was added to the cooled solution and the mixture stirred at 20° C. for 2 h [until a sample spotted on a tlc plate no longer showed the formation of yellow dimethyl (4-amino-2-nitrophenyl) malonate]. The mixture was then evaporated and the residue was distilled in a Kugelrohr (1 mm Hg, 90° C.) to remove excess benzyl alcohol. Flash chromatography on silca gel, eluting with petroleum ether/EtOAc (3:1) gave dimethyl [4-(benzyloxycarbonyl)amino-2-nitrophenyl]malonate as a yellow oil (3.77 g, 81%). $^1$H NMR (CDCl$_3$) 8.16 (d, J=2.3 Hz, 1 H, H-3), 7.59 (dd, J=8.5, 2.3 Hz, 1 H, H-5), 7.42–7.33 (m, 6 H, H-6 and Ph), 7.11 (s, 1 H, NH), 5.25 (s, 1 H, ArCH), 5.22 (s, 2 H, OCH$_2$Ph), 3.78 (s, 6 H, CO$_2$Me); $^{13}$C NMR (CDCl$_3$) d 167.9, (CO$_2$Me), 152.8 (NCO$_2$), 149.0, 139.1, 135.4, 131.9, 128.7, 128.6, 128.4, 122.7, 121.9, 114.6 (aromatic C), 67.6 (OCH$_2$Ph), 53.5 (ArCH), 53.2 (OMe); MS (DEI) m/z 402 (2%, M$^+$), 91 (100%, C$_7$H$_7$); HRMS calcd. for $C_{19}H_{18}N_2O_8$ 402.10631, found 402.10594.

A solution of the above 2-nitrophenylmalonate (3.12 g, 7.75 mmol) in THF (80 mL) was added dropwise over 30 min to a solution of diisobutylaluminium hydride (93 mL of a 1M solution in hexanes, 93 mmol) in THF (100 mL) under nitrogen, with cooling in an ice-salt bath (maintaining the internal temperature at −7 to 0° C.). The mixture was allowed to warm to 20° C. over 1 h, then poured into ice-cold aqqueous HCl (3 N, 260 mL). The THF was evaporated, the aqueous residue was extracted with EtOAc (×3), and the extracts dried ($Na_2SO_4$) and evaporated. Dry column chromatography on silica gel, eluting with EtOAc/ petroleum ether (1:3 then 1:1 then 2:1) gave recovered dimethyl [4-(benzyloxycarbonyl)amino-2-nitrophenyl] malonate (0.42 g, 13%) and 2-[4-(benzyloxycarbonyl) amino-2-nitrophenyl]propane-1,3-diol as a light brown foam (1.35 g, 50%). A sample of the latter was crystallized from CHCl$_3$, giving pale yellow flakes, mp 119–121° C. $^1$H NMR ((CD$_3$)$_2$SO) d 10.15 (s, 1 H, NH), 7.97 (d, J=2.2 Hz, 1 H, H-3), 7.60 (dd, J=8.6, 2.2 Hz, 1 H, H-5), 7.49 (d, J=8.6 Hz, 1 H, H-6), 7.45–7.33 (m, 5 H, Ph), 5.18 (s, 2 H, OCH$_2$Ph), 4.67 (t, J=5.3 Hz, 2 H, OH), 3.73–3.66 (m, 2 H, CHHOH), 3.63–3.56 (m, 2 H, CHHOH), 3.23 (p, J 6.4 Hz, 1 H, ArCH); $^{13}$C NMR ((CD$_3$)$_2$SO) d 153.3 (NCO$_2$), 150.9, 137.8, 136.2, 129.0 (C-1,2,4 and i C of Ph), 129.9, 121.7, 112.3 C-3,5,6), 128.4, 128.11, 128.09, (o, m, p C of Ph), 66.1 (OCH$_2$Ph), 61.8 (CH$_2$OH), 44.1 (ArCH). Anal. Calculated for $C_{17}H_{18}N_2O_6$: C, 59.0; H, 5.2; N, 8.1. Found: (C, 58.9; H, 5.4; N, 8.3%.

A solution of the above nitrodiol (1.02 g, 2.9 mmol) in EtOH (80 mL) with PtO$_2$ (0.12 g) was hydrogenated at 50 psi and 20° C. for 50 min, filtered through Celite, and evaporated. Dry column chromatography on silica gel, eluting, with EtOAc/MeOH (20:1 then 10:1) gave 2-[2-amino-4-(benzyloxycarbonyl)aminophenyl]propane-1,3-diol as a very pale yellow oil (0.88 g, 94%). $^1$H NMR ((CD$_3$)$_2$SO) d 9.36 (s, 1 H, NH), 7.43–7.30 (m, 5 H, Ph), 6.82 (d, J=2 Hz, 1 H, H-3), 6.81 (d, J=8.3 Hz, 1 H, H-6), 6.58 (dd, J=8.3, 2.1 Hz, 1 H, H-5), 5.12 (s, 2 H, OCH$_2$Ph), 4.82 (s, 2 H, NH$_2$ or OH), 4.50 (s, 2 H NH$_2$ or OH), 3.69–3.62 (m, 2 H, CHHOH), 3.54–3.46 (m, 2 H, CHHOH), 2.83 (p, J=6.2 Hz, 1 H, ArCH); $^{13}$C NMR ((CD$_3$)$_2$SO) d 153.2 (NCO$_2$), 146.8, 137.2, 136.8, 120.4 (C-1,2,4 and i C of Ph), 128.3, 127.92, 127.86 (o, m, p C of Ph), 127.0, 107.2, 105.2 (C-3,5,6), 65.3 (OCH$_2$Ph), 62.3 (CH$_2$OH), 43.2 (ArCH); MS (DEI) m/z 316 (30%, M$^+$), 285 (30%, M—CH$_2$OH), 91 (100%, C$_7$H$_7$); HRMS calcd. for $C_{17}H_{20}N_2O_4$ 316.14231, found 316.14182.

A solution of the above aminodiol (0.70 g, 2.21 mmol), di-t-butyldicarbonate (0.53 g, 2.4 mmol) and Na$_2$CO$_3$ (0.26 g, 2.4 mmol) in THF (120 mL) and water (60 mL) was stirred at 20° C. More di-t-butyldicarbonate (2×0.53 g) was; added after 5 and 8 days, with sufficient THF and water to maintain a single phase. After 14 days the THF was evaporated, the aqueous layer extracted with EtOAc (×2), and the organic extracts dried (Na$_2$SO$_4$) and evaporated. Dry column chromatography on silica gel, eluting with EtOAc/ petroleum ether (2:1 then 4:1) gave 2-[4-(benzyloxycarbonyl)amino-2-(t-butyloxycarbonyl) aminophenyl]propane-1,3-diol as a white foam (0.78 g, 85%). $^1$H NMR [(CD$_3$)$_2$SO] d 9.67 (s, 1 H, NH), 8.62 (s, 1 H, NH), 7.60 (s, 1 H, H-3), 7.44–7.31 (m, 5 H, Ph), 7.19 (dd, J=8.5, 1.7 Hz, 1 H, H-5), 7.08 (d, J=8.5 Hz, 1 H, H-6), 5.14 (s, 2 H, OCH$_2$Ph), 4.84 (t, J=4.7 Hz, 2 H, OH), 3.78–3.70 (m, 2 H, CHHOH), 3.54–3.45 (m, 2 H, CHHOH), 2.98 (p, J=6.3 Hz, 1 H, ArCH), 1.45 (s, 9 H, t-Bu). $^{13}$C NMR d 153.3 (resolves into two peaks on D$_2$O exchange, 2×NCO$_2$), 137.1, 137.0, 136.7, 129.4 (C-1,2,4 and i C of Ph), 128.4, 127.91, 127.87 (o, m, p C of Ph), 127.4, 114.6, 114.4 (C-3,5,6), 78.8 (OCMe$_3$), 65.5 (OCH$_2$Ph), 62.8 (CH$_2$OH), 43.9 (ArCH), 28.1 (C(CH$_3$)$_3$); MS (DEI) m/z 416 (2%, M$^+$), 91 (100%, C$_7$H$_7$); HRMS calcd. for $C_{22}H_{28}N_2O_6$ 416.19474, found 416.19544.

Diethylazodicarboxylate (0.47 mL, 3.0 mmol) was added dropwise over 5 min to a solution of the above t-butyloxycarbonyl diol (0.74 g, 1.78 mmol) and triphenylphosphine (0.84 g, 3.2 mmol) in THF (60 mL) under nitrogen and the mixture stirred at 20° C. After 10 min the mixture was diluted with EtOAc, washed with aqqueous NaCl, and the organic phase dried (Na$_2$SO$_4$) and evaporated. Dry column chromatography on silica gel, eluting with EtOAc/petroleum ether (1:2) gave an overlapping band of reduced diethylazodicarboxylate and 6-[(benzyloxycarbonyl)amino]-1-(t-butyloxycarbonyl)-3-(hydroxymethyl)indoline. A small fraction of the product was obtained in a pure state as a very pale yellow oil. $^1$H NMR ((CD$_3$)$_2$SO) d 9.68 (s, 1 H, NH), 7.97 (br s, 1 H, H-7), 7.44–7.31 (m, 5 H, Ph), 7.11 (d, J=8.1 Hz, 1 H, H-4), 6.98 (br d, J=8 Hz, 1 H, H-5), 5.13 (s, 2 H, OCH$_2$Ph), 4.90 (t, J=5.0 Hz, 1 H, OH), 3.94 (apparent t, J=10.3 Hz, 1 H, NCHH), 3.75 (dd, J=11.3, 5.1 Hz, 1 H, NCHH), 3.61–3.54 (m, collapses to dd, J=10.2, 4.7 Hz in D$_2$O exchange, 1 H, CHHOH), 3.41–3.28 (m, 2 H, ArCHCHHOH), 1.51 (s, 9 H, t-Bu); $^{13}$C NMR ((CD$_3$)$_2$SO) d 153.2, 151.6 (2×NCO$_2$), 143 (br, 138.6, 136.7, 126.4 (C-6,8,9 and i C of Ph), 128.3, 127.96, 127.90 (o, m, p C of Ph), 124.4, 112.1, 105.0 (C-4,5,7), 79.7 (OCMe$_3$), 65.5, 63.9 (OCH$_2$Ph, CH$_2$OH), 51.4 (C-2), 41.2 (C-3), 28.0 (C(CH$_3$)$_3$); MS (DEI) m/z 398 (4%, M$^+$); HRMS calcd. for C$_{22}$H$_{26}$N$_2$O$_5$ 398.18417, found 398.18402.

Methanesulfonyl chloride (0.25 mL, 3.2 mmol) was added to a solution of the mixture obtained from the previous reaction (ca. 1.8 mmol of alcohol) and Et$_3$N (0.50 mL, 3.6 mmol) in CH$_2$Cl$_2$ (60 mL) at 0° C., and the mixture was stirred for 15 min. Aqueous NaHCO$_3$ was added, the mixture was extracted with CH$_2$Cl$_2$ (×2) and the extracts dried (Na$_2$SO$_4$) and evaporated. Flash chromatography on silica gel, eluting with CHCl$_3$.EtOAc (20:1 then 10:1) gave 6-[(benzyloxycarbonyl)amino]-1-(t-butyloxycarbonyl)-3-[(methanesulfonyloxy)methyl]indoline as a white foam (0.79 g, 93% for two steps). $^1$H NMR (CDCl$_3$) d 7.73 (s, 1 H, H-7), 7.41–7.3 1 (m, 5 H, Ph), 7.12 (d, J=8.1 Hz, 1 H, H-4), 6.73 (s, 1 H, H-5), 5.19 (s, 2 H, OCH$_2$Ph), 4.32 (dd, J=9.9, 5.5 Hz, 1 H, CHHOSO$_2$Me), 4.18 (dd, J=9.9, 8.1 Hz, 1 H, CHHOSO$_2$Me), 4.11–4.02 (m, 1 H, NCHH), 3.92–3.84 (m, 1 H, NCHH), 3.72–3.62 (m, 1 H, H-3), 2.96 (s, 3 H, OSO$_2$Me), 1.56 (s, 9 H, t-Bu); $^{13}$C NMR (CDCl$_3$) d 153.2, 152.1 (2×NCO$_2$), 143.9, 138.7, 136.0, 123.6 (C-6,8,9 and i C of Ph), 128.6, 128.3 (br) (o, m, p C of Ph), 124.9, 112.7, 105.9 (C-4,5,7), 81.2 (OCMe$_3$), 71.0 (CH$_2$OSO$_2$), 67.0 (OCH$_2$Ph), 51.1 (C-2), 39.1 (C-3), 37.5 (OSO$_2$CH$_3$), 28.4 (C(CH$_3$)$_3$); MS (DEI) m/z 476 (5%, M$^+$), 91 (100%, C$_7$H$_7$); HRMS calcd. for C$_{23}$H$_{28}$N$_2$O$_7$S 476.16172, found 476.16070.

The above benzyloxycarbonylaminoindoline (306 mg, 0.64 mmol) was stirred in HCl-saturated EtOAc (10 mL) at 20° C. for 1 h (until tlc indicated complete reaction) and the mixture was evaporated. 1-(3-Dimethylaminopropyl)-3-ethylcarbodiimide hydrochloride (EDCI, 0.37 g, 1.9 mmol) and 5,6,7-trimethoxyindole-2-carboxylic acid [Y. Fukuda, Y. Itoh, K. Nakatani, and S. Terashima, *Tetrahedron*, 1994, 50, 2793–2808] (161 mg, 0.64 mmol) in DMF (15 mL) were added to the crude indoline hydrochloride, and the mixture stirred at 20° C. under nitrogen for 22 h. The DMF was evaporated, the residue was dissolved in EtOAc and water, extracted once more with EtOAc, and the organic extracts were dried (Na$_2$SO$_4$) and evaporated. Dry column chromatography of the residue on silica gel, eluting with EtOAc/petroleum ether (1:1), gave 6-[(benzyloxycarbonyl)amino]-3-[(methanesulfonyloxy)methyl]-1-[(5',6',7'-trimethoxyindol-2'-yl)carbonyl]indoline as a pale pink crystalline solid (209 mg, 53%), mp (EtOAc/petroleum ether) 153–154° C. $^1$H NMR ((CD$_3$)$_2$SO) d 11.44 (s, 1 H, indole NH), 9.85 (s, 1 H, carbamate NH), 8.38 (s, 1 H, H-7), 7.46–7.33 (m, 5 H, Ph), 7.33 (d, J=8.2 Hz, 1 H, H-4), 7.25 (dd, J=8.2, 1.8 Hz, 1 H, H-5), 7.03 (d, J=1.9 Hz, 1 H, H-3'), 6.95 (s, 1 H, H-4'), 5.15 (s, 2 H, OCH$_2$Ph), 4.62 (apparent t, J=10 Hz, 1 H, CH$_2$), 4.45 (dd, J=9.8, 5.1 Hz, 1 H, CH$_2$), 4.35 (dd, J=9.8, 7.2 Hz, 1 H, CH$_2$), 4.27 (dd, J=10.9, 5.3 Hz, 1 H, CH$_2$), 3.93 (s, 3 H, OCH$_3$), 3.87–3.80 (m, 1 H, H-3), 3.81 (s, 3 H, OCH$_3$), 3.80 (s, 3 H, OCH$_3$), 3.18 (s, 3 H, OSO$_2$Me). $^{13}$C NMR d 160.1, 153.3, 149.1, 144.0, 139.8, 139.1, 139.0, 136.6, 130.8, 124 6, 123.1 (C-6,8,9,2',5',6',7',8',9', i C of Ph, NCO, NCO$_2$, one peak not observed), 128.4, 128.0, 127.9 (o, m, p C of Ph), 125.3, 113.9, 107.7, 106.1, 98.0 (C-4,5,7,3',4'), 71.3 (CH$_2$OSO$_2$), 65.6 (OCH$_2$Ph), 61.0, 60.9, 55.9 (3×OCH$_3$), 53.0 (C-2), 39.3 (C-3), 36.5 (OSO$_2$CH$_3$). Anal. Calculated for C$_{30}$H$_{31}$N$_3$O$_9$S.0.5EtOAc: C, 58.8; H, 5.4; N, 6.4. Found: C, 58.7; H, 5.3; N, 6.6%.

A solution of ammonium formate (0.24 g, 3.8 mmol) in water (12 mL) was added to the above 6-[(benzyloxycarbonyl)indoline (233 mg, 0.38 mmol) and Pd/C (5%, 100 mg) in THF (50 mL) and the mixture was stirred at 20° C. More Pd/C (30 mg) was added after 70 min, and after 100 min (tlc indicates complete reaction) the catalyst was filtered off and washed with EtOAc. The filtrate was diluted with aq. NaCl, extracted with EtOAc (×2), and the extracts dried (Na$_2$SO$_4$) and evaporated. Dry column chromatography (eluting with 2:1 EtOAc:petroleum ether) gave 6-amino-3-[(methanesulfonyloxy)-methyl]-1-[(5',6',7'-trimethoxyindol-2'-yl)carbonyl]indoline (25) as a pale yellow foam (154 mg, 85%). This mesylate (150 mg, 0.32 mmol) and LiCl (0.13 g, 3.2 mmol) were stirred in DMF (5 mL) at 70° C. under nitrogen for 80 min, and the DMF evaporated. The residue was dissolved in EtOAc and water, extracted once more with EtOAc, and the organic extracts dried (Na$_2$SO$_4$) and evaporated. Dry column chromatography, eluting with EtOAc/petroleum ether (1:1) gave 6-amino-3-(chloromethyl)-1-[(5',6',7'-trimethoxyindol-2'-yl)carbonyl]indoline (32) (87 mg, 66%), mp (EtOAc/Et$_2$O) 173–174° C. $^1$H NMR [(CD$_3$)$_2$SO] δ 11.36 (d, J=1.6 Hz, 1 H, NH), 7.44 (br s, 1 H, H-7), 7.05 (d, J=8.0 Hz, 1 H, H-4), 6.96 (d, J=2.1 Hz, 1 H, H-3'), 6.95 (s, 1 H, H-4'), 6.30 (dd, J=8.0, 2.2 Hz, 1 H, H-5), 5.18 (s, 2 H, NH$_2$), 4.54 (dd, J=10.8, 8.7 Hz, 1 H, NCHH), 4.20 (dd, J=10.8, 4.4 Hz, 1 H, NCHH), 3.93 (s, 3 H, OCH$_3$), 3.91 (dd, J=9.9, 3.5 Hz, 1 H, CHHCl), 3.81 (s, 3 H, OCH$_3$), 3.79 (s, 3 H, OCH$_3$), 3.74–3.60 (m, 2 H, CHCHHCl). $^{13}$C NMR δ 159.9, 149.0, 144.2, 139.6, 139.0, 131.2, 125.1, 123.1, 118.8 (C-6,8,9,2',5',6',7',8',9', NCO, one peak not observed), 124.7, 109.5, 105.6, 102.9, 98.0 (C-4,5,7,3',4'), 61.0, 60.9, 55.9 (3×OCH$_3$), 54.5 (C-2), 47.9 (CH$_2$Cl), 41.8 (C-3). Anal. Calculated for C$_{12}$H$_{22}$ClN$_3$O$_4$): C, 60.7; H, 5.3; N, 10.1. Found: C, 60.7; H, 5.4; N, 9.8%.

INDUSTRIAL APPLICATION

As will be apparent from the above description and examples, this invention provides improved methods for cancer therapy. The advantages of the invention are largely achieved through the selection and use of RACP.

RACP retain the selectivity of BD for hypoxic microenvironments but provide the following additional advantages:

(a) Reduction is confined to the radiation field, greatly diminishing systemic toxicity. This feature takes advantage of recent technological advances in computerised radiation treatment planning and delivery systems which now offer high-precision matching of the radiation field contours to the tumour in three dimensions (conformal treatment).

(b) The forward reduction is inhibited in oxic cells. The very rapid reaction of the major reducing species generated by radiolysis of water, $e_{aq}^-$ and H., with O$_2$ would ensure that the rate of forward reduction is greatly diminished in the presence of O$_2$. In contrast, the rate of the forward reduction by bioreductive enzymes is probably insensitive to O$_2$ in most cases, the inhibition of net reduction being due only to back-oxidation by O$_2$. For the RAC mechanismn, O$_2$ can inhibit the forward reduction, as well as reoxidising the one-electron product, and is therefore expected to provide greater inhibition by $O_2$ (hypoxic selectivity) than achieved with BD.

(c) There is no competing two-electron ($O_2$-insensitive) reduction by radiolytic reduction since this is an obligate one-electron process, further enhancing selectivity relative to enzymatic activation.

(d) Activation would be independent of the peculiarities of reductive enzyme expression of the tumour.

(e) It would be possible to use high dose rate irradiation to lower $O_2$ concentrations further. The (enzymatic) activation of some BD is so readily inhibited by traces of $O_2$ that many radiobiologically hypoxic cells may not be sensitive. RAC are expected to be at least as sensitive to trace $O_2$ ((b) above), but delivery of the radiation at a high dose rate (ca 5 $Gy.s^{-1}$) would scavenge sufficient $O_2$ to make radiobiologically hypoxic tissue (<1 $\mu M$ $O_2$) completely anoxic during the irradiation period.

Those persons skilled in the art will understand that the specific description provided above is exemplary only and that the present invention is not limited thereto.

What is claimed is:

1. A method of treating neoplastic disease which comprises the steps of:

(a) administering to a patient in need of such treatment an effective amount of a radiation-activated cytotoxin prodrug (RACP) which has low toxicity, which is reducible by reducing agents generated by the radiolysis of water and which, upon reduction, releases a sufficient amount of a cytotoxic effector of sufficient cytotoxic potency to kill tumor cells, wherein the RACP is a compound of formula I

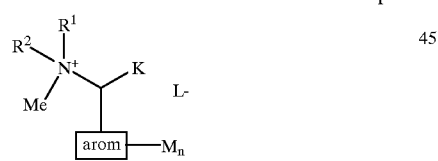

wherein $R^1$ represents H or $C_1$–$C_4$ alkyl unsubstituted or substituted with hydroxyl, ether, amino, methylamino or dimethylamino groups;

n is 0, 1 or 2, and each M is independently selected from $NO_2$, $CF_3$, $CH_2OR^1$, $COR^1$, $CONHR^1$, $OR^1$, $NR^1R^1$ and $SO_2R^1$ wherein $R^1$ is as defined above;

wherein arom is a single benzene ring or a 5- or 6-membered aromatic heterocycle containing one or two heteroatoms independently selected from O, S and N;

L– is a pharmacologically acceptable counterion;

K is H or Me;

and wherein $R^2$ is represented by:

(i) a radical of formula II

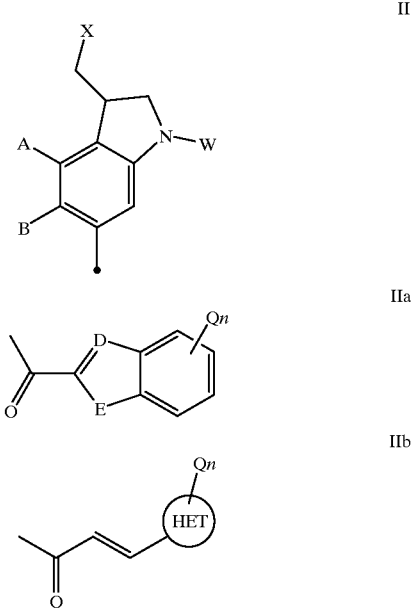

where X is halogen or $OSO_2R^1$ (where $R^1$ is as defined above);

A and B are each H or collectively represent an unsubstituted or substituted fused benzene or pyrrole ring;

W is selected from $SO_2R^1$ (where $R^1$ is as defined above) and the structures IIa and IIb, where:

D is CH or N;

E is NH or O;

each Q is independently selected from $OR^1$ and $NR^1R^1$ wherein $R^1$ is as defined above;

n is 0, 1, 2 or 3; and

HET represents a 5- or 6-membered carbocycle or heterocycle containing one or two heteroatoms independently selected from O, S, and N;

(ii) a radical of formula III

III where X, A, B, Q and n are as defined above; and each D is independently CH or N; and each E is independently NH or O;

(iii) a radical of formula IV

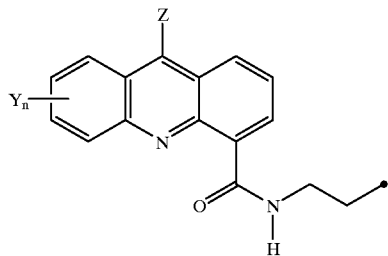

where Z is H or NHR$^1$ (where R$^1$ is as defined above);

n is 0, 1 2, or 3; and each Y is independently selected from Me and OMe; or (iv) a radical of formula V

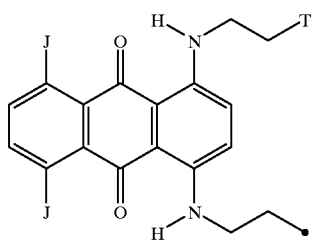

where each J is independently H or OH; and T is NMe$_2$, or a moiety of the formula

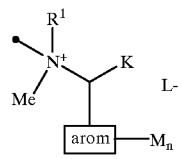

wherein n, M, arom, K and R$^1$ are as defined for formula I above; and (b) irradiating said tumor cells with ionizing radiation to reduce the prodrug which is present at the locus of said tumor cells to release said cytotoxic effector.

2. A method as claimed in claim 1 wherein the RACP is a compound of formula I wherein R$^2$ is a radical of formula II.

3. A method as claimed in claim 1 wherein the RACP is a compound of formula I wherein R$^2$ is a radical of formula III.

4. A method as claimed in claim 1 wherein the RACP is a compound of formula I wherein R$^2$ is a radical of formula IV.

5. A method as claimed in claim 1 wherein the RACP is a compound of formula I wherein R$^2$ is a radical of formula V.

6. A method as claimed in claim 1 wherein the RACP is a compound of formula Ia

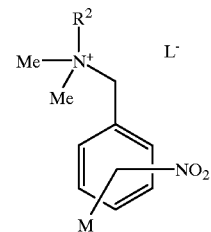

wherein R$^2$ and L- are defined as in claim 2 and M is one of H, CF$_3$, CH$_2$OR$^1$, COR$^1$, CONHR$^1$, OR$^1$, NR$^1$R$^1$ and SO$_2$R$^1$ where R$^1$ represents H or C$_1$–C$_4$ alkyl unsubstituted or substituted with hydroxyl, ether, amino, methylamino or dimethylamino groups.

7. A method of treating neoplastic disease which comprises the steps of:

(a) administering to a patient in need of such treatment an effective amount of a radiation-activated cytotoxin prodrug (RACP) which has low toxicity, which is reducible by reducing agents generated by the radiolysis of water and which, upon reduction, releases a sufficient amount of a cytotoxic effector of sufficient cytotoxic potency to kill tumor cells wherein the RACP is a compound of formula (VI)

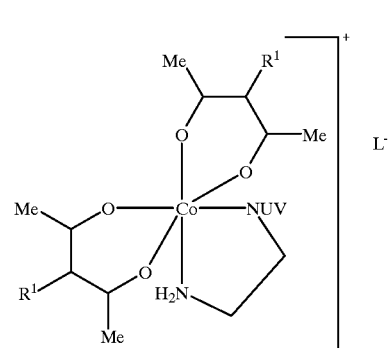

wherein each R$^1$ is independently H or C$_1$–C$_4$ alkyl unsubstituted or substituted with hydroxyl, ether, amino, methylamino or dimethylamino groups;

U and V are both CH$_2$CH$_2$Cl, or U is H and V is a radical of formula II

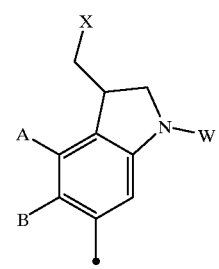

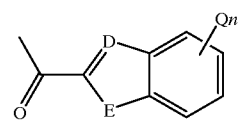

IIb

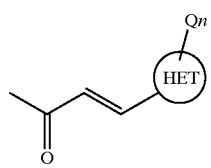

wherein X is halogen or $OSO_2R^1$ (where $R^1$ is as defined above);

A and B are each H or collectively represent an optionally substituted fused benzene or pyrrole ring;

W is selected from $SO_2R^1$ (wherein $R^1$ is as defined above) and the structures IIa and IIb, where:

D is CH or N;

E is NH or O;

each Q is independently selected from $OR^1$ and $NR^1R^1$ wherein $R^1$ is as defined above;

n is 0, 1, 2 or 3; and

HET represents a 5- or 6-membered carbocycle or heterocycle containing one or two heteroatoms independently selected from O, S and N; or a radical of formula III

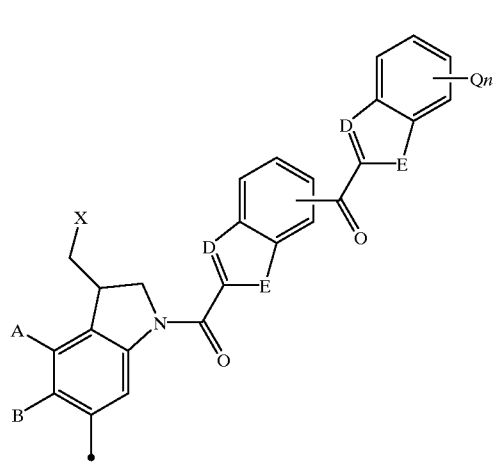

III where X, A, B, Q and n are as defined above; and each D is independently CH or N; and each E is independently NH or O;

and L– is a pharmaceutically acceptable anion; and (b) irradiating said tumor cells with ionizing radiation to reduce the prodrug which is present at the locus of said tumor cells to release said cytotoxic effector.

8. A method as claimed in claim 7 wherein the RACP is bis(3-methyl-2,4-pentanedionato)(N,N-bis(2-chloroethyl)ethylenediamine)cobalt (III) chloride.

9. A method of treating neoplastic disease which comprises the steps of (a) administering to a patient in need of such treatment an effective amount of a radiation-activated cytotoxin prodrug (RACP) which has low toxicity, which is reducible by reducing agents generated by the radiolysis of water and which, upon reduction, releases a sufficient amount of a cytotoxic effector of sufficient cytotoxic potency to kill tumor cells, wherein the RACP is a compound of formula VII:

VII

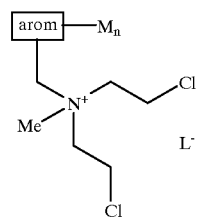

wherein n is 0, 1 or 2, and each M is independently selected from the group consisting of $NO_2$, $CF_3$, $CH_2OR^1$, $COR^1$, $CONHR^1$, $OR^1$, $NR^1R^1$ and $SO_2R^1$ wherein $R^1$ represents H or $C_1$–$C_4$ alkyl optionally substituted with hydroxyl, ether, amino, methylamino, or dimethylamino groups; and arom is a single benzene ring or a five- or six-membered aromatic heterocycle containing one or two heteroatoms independently selected from the group consisting of O, S and N; and L– is a pharmacologically acceptable counterion;

(b) irradiating said tumor cells with ionizing radiation to reduce the prodrug which is present at the locus of said tumor cells to release said cytotoxic effector.

10. A method as claimed in claim 9 wherein the RACP is selected from the following compounds:

N,N-bis(2-chloroethyl)-N-methyl-N-[(1-methyl-4-nitro-5-imidazolyl)-methyl]ammonium chloride, N,N-bis(2-chloroethyl-N-methyl-N-(2-nitrobenzyl)ammonium chloride, N,N-bis(2-chloroethyl-N-methyl-N-(3-nitrobenzyl)ammonium chloride, N,N-bis(2-chloroethyl-N-methyl-N-(4-nitrobenzyl)ammonium chloride, N,N-bis(2-chloroethyl-N-methyl-N-(4-methylsulfonyl)benzyl)ammonium chloride, and N,N-bis(2-chloroethyl-N-methyl-N-benzylammonium chloride.

11. A method of treating neoplastic disease which comprises the steps of:

(a) administering to a patient in need of such treatment an effective amount of a radiation-activated cytotoxin prodrug (RACP) which has low toxicity, which is reducible by reducing agents generated by the radiolysis of water and which, upon reduction, releases a sufficient amount of a cytotoxic effector of sufficient cytotoxic potency to kill tumor cells wherein the RACP is a compound of formula (VIII)

VIII

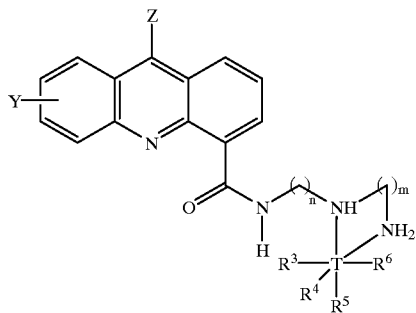

wherein Y and Z are as defined for formula IV, T is Co(III) or Cr(III), n is from 2 to 6, m is 2 or 3, and $R^3$, $R^4$, $R^5$ and $R^6$ are each independently selected from CN, halogen, SCN, H$_2$O and NHR$^1$ wherein R$^1$ is as defined in claim 2, or together represent 3-R$^7$acetonylacetonato where R$^7$ is H, Me, NO$_2$, CN, SCN or SPh where Ph is a benzene ring unsubstituted or substituted with up to two groups independently selected from Me, OMe, NO$_2$ and NMe$_2$); and (b) irradiating said tumor cells with ionizing radiation to reduce the prodrug which is present at the locus of said tumor cells to release said cytotoxic effector.

12. A compound of formula I:

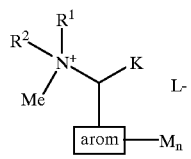

I wherein R$^1$ represents H or C$_1$–C$_4$ alkyl optionally substituted with hydroxyl, ether, amino, methylamino or dimethylamino groups;

n is 0, 1 or 2, and each M is independently selected from NO$_2$, CF$_3$, CH$_2$OR$^1$, COR$^1$, CONHR$^1$, OR$^1$, NR$^1$R$^1$ and SO$_2$R$^1$ wherein R$^1$ is as defined above;

wherein arom is a single benzene ring or a 5- or 6-membered aromatic heterocycle containing one or two heteroatoms independently selected from O, S and N;

L$^-$ is a pharmacologically acceptable counterion;

K is H or Me;

and wherein R$^2$ is represented by:

(i) a radical of formula II

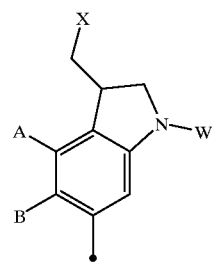

II

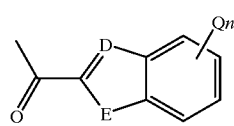

IIa

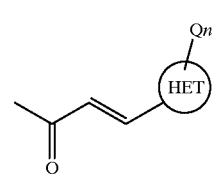

IIb where X is halogen or OSO$_2$R$^1$ (where R$^1$ is as defined above);

A and B are each H or collectively represent an unsubstituted or substituted fused benzene or pyrrole ring;

W is selected from SO$_2$R$^1$ (where R$^1$ is as defined above) and the structures IIa and IIb, where:

D is CH or N;

E is NH or O;

each Q is independently selected from OR$^1$ and NR$^1$R$^1$ wherein R$^1$ is as defined above;

n is 0, 1, 2 or 3; and

HET represents a 5- or 6-membered carbocycle or heterocycle containing one or two heteroatoms independently selected from O, S and N;

(ii) a radical of formula III

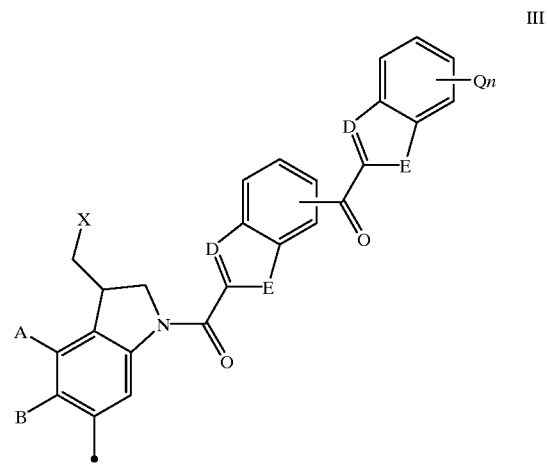

III where X, A, B, Q and n are as defined above; and each D is independently CH or N; and each E is independently NH or O;

(iii) a radical of formula IV

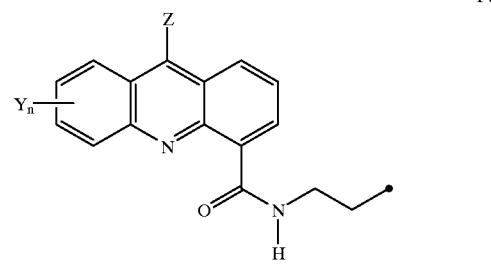

IV where Z is H or NHR$^1$ (where R$^1$ is as defined above);

n is 0, 1, 2 or 3; and each Y is independently selected from Me and OMe; or (iv) a radical of formula V

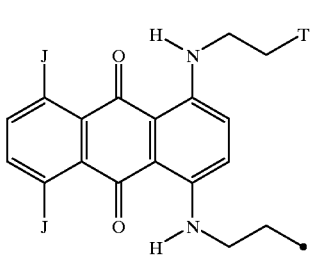

V where each J is independently H or OH; and

T is NMe₂ or a moiety of formula

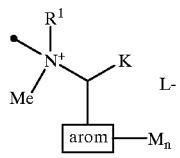

wherein n, M, arom, K and R¹ are as defined for formula I above.

13. A compound of formula I as claimed in claim 12 wherein R² is a radical of formula II.

14. A compound as claimed in claim 13 wherein the compound is selected from the following:
   3-(chloromethyl)-6-[N,N-dimethyl-N-(4-nitrobenzyl)-ammonio]-1-[(5',6',7'-trimethoxyindol-2'-yl)carbonyl]indoline chloride, and
   3-(chloromethyl)-6-[N,N-dimethyl-N-(2-nitrobenzyl)-ammonio]-1-[(5',6',7'-trimethoxyindol-2'-yl)carbonyl]indoline chloride.

15. A compound of formula I as claimed in claim 12 wherein R² is a radical of formula III.

16. A compound of formula I as claimed in claim 12 wherein R² is a radical of formula IV.

17. A compound as claimed in claim 16 wherein the compound is selected from the following:
   2-[N-(acridin-4-yl)carbonyl]aminoethyl-(dimethyl)-4-nitrobenzylammonium bromide,
   2-[N-(acridin-4-yl)carbonyl]aminoethyl-(dimethyl)-(5-nitro-2-thienyl)methylammonium chloride,
   2-[N-(9-amino-5-methylacridin-4-yl)carbonyl]aminoethyl-(dimethyl)-4-nitrobenzylammonium bromide,
   2-[N-(9-amino-5-methylacridin-4-yl)carbonyl]aminoethyl-(dimethyl)-2-nitrobenzyl]ammonium chloride,
   2-[N-(9-amino-5-methylacridin-4-yl)carbonyl]aminoethyl-(dimethyl)-5-nitro-2-thienylmethylammonium chloride,
   2-[N-(9-amino-5-methylacridin-4-yl)carbonyl]aminoethyl-(dimethyl)-2-[4-morpholino-5-nitro-4-thiazolylmethyl]ammonium chloride,
   2-(N-[9-amino-5-methylacridin-5-yl]carbonyl)aminoethyl-(dimethyl)[1-methyl-5-nitro-2-pyrrolyl]methylammonium chloride,
   2-(N-[9-amino-5-methylacridin-4-yl]carbonyl)aminoethyl-(dimethyl)-(1-methyl-4-nitro-5-imidazolyl)methylammonium chloride, and
   2-(N-[9-amino-5-methylacridin-4-yl]carbonyl)aminoethyl-(dimethyl)-(3-nitro-2-thienyl)methylammonium chloride.

18. A compound of formula I as claimed in claim 12 wherein R² is a radical of formula V.

19. A compound as claimed in claim 18 wherein the compound is selected from the following:
   1,4-bis[((2-(4-nitrobenzyl)dimethylammonium)-ethyl)amino]-9,10-anthracenedione dichloride,
   1-(2-(4-nitrobenzyl)dimethylaminoethylammonium)-4-(2-dimethylamino)ethylammino-9,10-anthracenedione acetate,
   1,4-bis[(2-(4-nitrobenzyl)dimethyl-ammonium)ethylamino]-5,8-dihydroxy-9,10-anthracenedione dichloride, and
   1-[(2-(4-nitrobenzyl)dimethylammonium)ethylamino]-4-[(2-dimethylamino)ethylamino]-5,8-dihydroxy-9,10-anthracenedione chloride.

20. A compound as claimed in claim 12 of formula Ia:

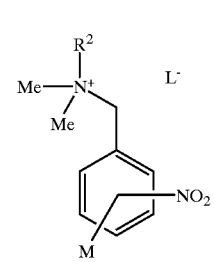

wherein R² and L⁻ are defined as in formula I, and M is one of H, $CF_3$, $CH_2OR^1$, $COR^1$, $CONHR^1$, $OR^1$, $NR^1R^1$ or $SO_2R^1$ where $R^1$ represents H or $C_1$–$C_4$ alkyl unsubstituted or substituted with hydroxyl, ether, amino, methylamino or dimethylamino groups.

21. A compound of formula VIII:

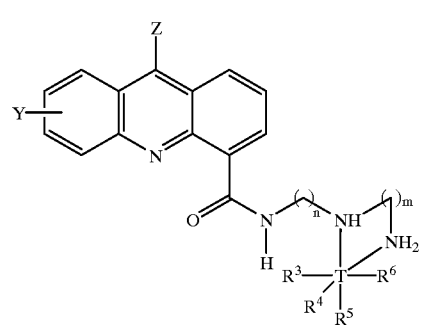

wherein Y and Z are as defined for formula IV, T is Co(III) or Cr(III), n is from 2 to 6, m is 2 or 3, and $R^3$, $R^4$, $R^5$ and $R^6$ are each independently selected from CN, halogen, SCN, $H_2O$ and $NHR^1$ wherein $R^1$ is as defined in claim 1, or together represent 3-$R^7$acetonylacetonato (where $R^7$ is H, Me, $NO_2$, CN, SCN or SPh).

22. A compound as claimed in claim 21 which is bis(3-methyl-2,4-pentanedionato)-(N-[3-[(2-aminoethyl)-amino]propyl]acridine-4-carboxamide)cobalt(III) perchlorate.

23. A pharmaceutical composition for use in treating neoplastic disease, comprising a RACP compound of the formula I or VIII, as defined in claim 1, and a pharmaceutically acceptable carrier or vehicle therefor.

24. A pharmaceutical composition as claimed in claim 23, wherein the RACP compound is a compound as defined above.

25. A pharmaceutical composition as claimed in claim 23, which is in an injectable form.

* * * * *